United States Patent
Todaro et al.

(10) Patent No.: US 6,171,824 B1
(45) Date of Patent: Jan. 9, 2001

(54) HYBRID CYTOKINES

(75) Inventors: George J. Todaro, Seattle; David W. Leung, Mercer Island; Timothy M. Rose, Seattle, all of WA (US)

(73) Assignee: Fred Hutchinson Cancer Research Center, Seattle, WA (US)

( * ) Notice: Under 35 U.S.C. 154(b), the term of this patent shall be extended for 0 days.

(21) Appl. No.: 08/149,101

(22) Filed: Nov. 8, 1993

Related U.S. Application Data

(63) Continuation-in-part of application No. 08/097,869, filed on Jul. 27, 1993, which is a continuation of application No. 07/753,178, filed on Aug. 30, 1991, now abandoned.

(51) Int. Cl.[7] ............... C12P 21/06; C07H 17/00; C07K 14/00
(52) U.S. Cl. ............ 435/69.5; 435/69.7; 435/320.1; 435/252.3; 536/23.4; 536/23.5; 536/23.51; 530/351
(58) Field of Search ............ 530/351; 536/23.4, 536/23.5, 23.51; 435/69.5, 69.7, 240.1, 320.1, 252.3

(56) References Cited

U.S. PATENT DOCUMENTS

| 4,935,233 | 6/1990 | Bell et al. ............. 424/85.5 |
| 5,371,193 | 12/1994 | Bennett et al. ............. 530/351 |

FOREIGN PATENT DOCUMENTS

| WO 90/12877 | 11/1990 | (WO) ............. C12N/15/62 |

OTHER PUBLICATIONS

Evans 1988. Science 240:889–895.*
Williams et al 1991 Cancer 67:2705–2707.*
Shanafelt et al. 1991 Embro J. 10:4105–4112.*
Rock et al. 1992 Protein Engineering 5:583–591.*
Yamamori et al. 1992 Neuroscience Res. 15:151–161.*
Rose et al., vol. 88, 1991, pp. 8641–8645, "Oncostayatin M is a Member of a Cytokine Family That Includes Leukemia–Inhibitory Factor, Granulocyte Colony–Stimulating Factor, and Interleukin 6".
Bazan et al., "Neuropoietic Cytokines in the Hematopoietic Fold", *Neuron*, vol. 7, pp. 197–208, Aug. 1991.
Malik et al., "Molecular Cloning, Sequence Analysis, and Functional Expression of a Novel Growth Regulator, Oncostatin M", *Molecular and Cellular Biology*, vol. 9, No. 7, pp. 2847–2853, Jul. 1989.
Yasukawa et al., *The EMBO Journal*. Structure and Expression of Human B Cell Stimulatory Factor-2 (BSF-2/IL-6) Gene. vol. 6, No. 10, pp. 2939–2945, Oct. 1987.
Malik et al., *Molecular and Cellular Biology*. vol. 9, No. 7, pp. 2847–2853, 1989.
Simpson et al., *FEBS*. Structural Characterization of a Murine Myeloid Leukemia Inhibitory Factor, 1988.

Musashi et al., *Cell Biology. Proc. Natl. Acad. Sci. USA*, vol. 38, pp. 765–769, Feb. 1991.
Bruce et al., *Progress in Growth Factor Research*. vol. 4, pp. 157–170, 1992.
Davis et al., *Science*. vol. 260, Jun. 18, 1993.
Williams & Park 1991, Hematopoietic Effects of a Granulocyte–Macrophage Colony–Stimulating Factor/Interleukin-3 Fusion Protein.
Unsicker et al., Neurobiology. Cytokines in Neural Regeneration. 2:671–678, 1992.
Lo, Donald C., *Proc. Natl. Acad. Sci. USA*. A Central Role for Ciliary Neurotrophic Factor? (Commentary). vol. 90 pp. 2557–2558, Apr., 1993.
Burstein, et al., *Journal of Cellular Physiology*. Leukemia Inhibitory Factor and Interleukin–11 Promote Maturation of Murine and Human Megakaryocytes In Vitro. 153:305–312, 1992.
Yang et al., *Biofactors*. Interleukin–11 and its Recepter. vol. 4, No. 1, pp. 15–21, 1992.
Ip et al., *Progress in Growth Factor Research*. Ciliary Neurotrophic Factor and Its Receptor Complex. vol. 4, pp. 139–155, 1992.
Paul et al., *Proc. Natl. Acad. Sci. USA*. Molecular Cloning of a cDNA Encoding Interleukin–11, A Stormal Cell–Derived Lymphopoietic and Hematopoietic Cytokine. vol. 87, pp. 7512–7516, Oct. 1990.
Kawashimia et al., *FEBS*. Molecular Cloning of cDNA Encoding Adipogenesis Inhibitory Factor and I Identity with Interleukin–11. vol. 283, No. 2, pp. 199–202, Jun., 1991.

(List continued on next page.)

Primary Examiner—Karen Cochrane Carlson
(74) Attorney, Agent, or Firm—Foley & Lardner

(57) ABSTRACT

Therapeutic hybrid cytokines, having a size ranging from about 10 to about 30 kDa, comprise portions of cytokines: leukemia inhibitory factor (LIF), granulocyte-colony stimulating factor (G-CSF), interleukin-6 (IL-6), interleukin-11 (IL-11), oncostatin-M (OSM), and ciliaryneurotrophic factor (CNTF). Hybrid cytokines comprise three or four α-helical sequences selected from α-helical sequences of IL-6, G-CSF, LIF, IL-11, CNTF and OSM and linking sequences of 5–40 amino acids in length, selected from the linking sequences of IL-6, G-CSF, LIF, IL-11, CNTF and OSM or other, desirable linking sequences. In the hybrid cytokines, at least one α-helical sequence is derived from a different cytokine than at least one other α-helical sequence; or, at least one linking sequence of a cytokine differentiates the hybrid cytokine from a corresponding cytokine. In hybrid cytokines having three α-helical sequences selected from the group of cytokines listed, a possible fourth sequence may not correspond to any α-helical sequence in any of the cytokines. Hybrid cytokines, radically different from any corresponding cytokines, have unexpected advantages in selective biological mechanisms over a much broader range of biological activities than exhibited by cytokines.

33 Claims, 5 Drawing Sheets

OTHER PUBLICATIONS

Hangoc et al., *Blood*, In Vivo Effects of Recombinant Interleukin–11 Myelopoiesis in Mice. vol. 81, No. 4, pp. 965–972, Feb., 1993.

Williams et al., *International Journal of Cell Cloning* . Hybrid Cytokines as Hematopoietic Growth Factors. 9:542–547, 1991.

Neben et al., *Blood*. Recombinnt Human Interleukin–11 Stimulates Megakaryocytopoiesis and Increases Peripheral Platelets in Normal and Splenectomized Mice. vol. 81, No. 4, pp. 901–908, Feb., 1993.

* cited by examiner

HYBRID CYTOKINES

CROSS REFERENCE TO RELATED APPLICATIONS

This is a Continuation-in-Part Application of U.S. application Ser. No. 08/097,869 filed Jul. 27, 1993, which is a Continuation Application of U.S. application Ser. No. 07/753,178, filed Aug. 30, 1991, now abandoned.

TECHNICAL FIELD

The invention concerns hybrid cytokines which have beneficial, therapeutic properties and comprise amino acid sequence components from cytokine family members leukemia inhibitory factor (LIF); granulocyte colony stimulating factor (G-CSF); interleukin-6 (IL-6); interleukin-11 (IL-11); ciliary neurotrophic factor (CNTF); and oncostatin-M (OSM).

BACKGROUND OF THE INVENTION

More than two dozen cytokines have been identified that regulate blood composition by controlling the growth and differentiation of hematopoietic stem cells. Interferons, tumor necrosis factor, stem cell factor, the numbered interleukins, ligands of oncogene receptors, and the various colony stimulating factors are exemplary of these proteins and glycoproteins. One of these factors, interleukin-6 (IL-6) was originally identified as a B-cell differentiation factor, but has subsequently been shown to induce acute phase protein synthesis in liver cells, to inhibit growth of certain myeloid leukemia cell lines and induce their differentiation into macrophage cells, to promote IL-3 dependent colony formation of primitive blast colony forming cells, to cause differentiation of neuronal cells, to enhance keratinocyte and mesangial cell growth, to promote the maturation of megakaryocytes, and to induce the proliferation and differentiation of T cells. In vivo, IL-6 increases the hematopoietic cell count of the erythroid, myeloid, and thrombocytic lineages. Other former names for IL-6 are β2-interferon, B-cell stimulatory factor-2, hybridoma/plasmacytoma growth factor, and monocyte granulocyte inducer type 2. The spectrum of activities attributable to IL-6 indicates that it is useful in tumor inhibition, bone remodeling, kidney development, and T- and B-cell proliferation and stimulation.

Interleukin-11 has been shown to augment hematopoietic proliferation and differentiation of cells from normal mice, increase B-cell maturation, augment macrphage proliferation and megakaryocyte maturation, proliferate multipotent hematopoietic progenitors, stimulate early murine progenitors, and inhibit adipogenesis. Burstein et al., *Journal of Cellular Physiology* (1992) 153:312; Bazan, *Neuron* (1991) 7:197; and Yang et al., *BioFactors* (1992) 4:15–21.

Ciliary neurotrophic factor (CNTF) receptor is most homologous to the IL-6 receptor and lacks a cytoplasmic domain. Except for skeletal muscle, peripheral (sciatic) nerve and adrenal gland, CNTF receptor expression appears confined to the central nervous system. CNTF has been shown to promote neuronal differentiation and neuron augmentation. Research results implicate CNTF in the trophic support of a broad range of peripheral and central neurons, broader in fact, than that of the neurotrophins. Lo, *Proc. Natl. Acad. Sci. USA* (1993) 90; 2557–2558. Specifically, CNTF has shown "rescue" effects on embryonic spinal cord motor neurons, axotomized facial motor neurons in young rats and degenerative motor neurons in mouse mutant progressive motor neuropathy. In vivo, CNTF infused into the lateral ventrical of fimbria-fornix-lesioned adult rats prevents degeneration of almost all septal neurons including many non-cholinergic neurons that are not maintained by nerve growth factor. Unsicker et al., *Neurobiology* (1992) 2:671–678.

Leukemia inhibitory factor (LIF) has been demonstrated to inhibit the growth of certain myeloid leukemia cells and to induce their differentiation into macrophage cells; to enhance interleukin-3 dependent colony formation of primitive blast cells; to promote megakaryocyte growth and differentiation; to induce neuronal differentiation; to stimulate the production of acute phase proteins and hepatocytes (all properties it shares with IL-6) and to inhibit the differentiation of embryonic stem cells and kidney cells and to induce bone resorption.

Oncostatin-M (OSM) is known to be a tumor inhibitor for melanoma and certain carcinoma cells and inhibits the growth of human A375 melanoma cells but not normal human fibroblasts. It is also an inhibitor of the growth of M1 myeloid leukemic cells and induces their differentiation into macrophage-like cells as well as stimulating megakaryocyte production in the spleen. OSM is also known to inhibit embryonic stem cell differentiation, induce hepatic cell acute-phase protein sythesis, induce mitosis of AIDS-related Kaposi's sarcoma cell and vascular smooth muscle cell and induce neuronal differentiation.

Granulocyte colony stimulating factor (G-CSF) stimulates neutrophil proliferation and differentiation and induces the differentiation of M1 murine myeloid leukemic cells into macrophage-like cells as well as enhancing interleukin-3 dependent colony formation of primitive blast cells. It appears to have little effect on the hematopoietic cell lineages of megakaryocytes or platelets but enhances cytosine arabinoside-mediated cytoxicity in human myeloid leukemia cells.

Reported biological activities of the foregoing cytokine family members are summarized in the following table:

TABLE I

Reported Biological Activities of Cytokine Family Members

|  | LIF | OSM | G-CSF | IL-6 | L-11 | CNTF |
|---|---|---|---|---|---|---|
| Endothelial Cell Proliferation | NR | + | NR | NR | NR | NR |
| Tumor Inhibition | + | + | NR | + | NR | NR |
| Embryonic Stem Cell Maintenance | + | + | NR | NR | NR | NR |
| Hematopoietic Leukemic Cell Differentiation | + | + | + | + | + | NR |
| Melanoma Cell Inhibition | − | + | − | + | NR | NR |
| Neutrophil Proliferation/Stimulation | NR | NR | + | + | + | NR |
| Myoblast Proliferation | + | NR | NR | NR | NR | NR |

TABLE I-continued

Reported Biological Activities of Cytokine Family Members

|  | LIF | OSM | G-CSF | IL-6 | L-11 | CNTF |
|---|---|---|---|---|---|---|
| Bone Remodeling | + | NR | NR | + | NR | NR |
| Kidney Development | + | NR | NR | NR | NR | NR |
| Neuronal Differentiation | + | + | NR | + | NR | + |
| Hepatocyte Stimulation | + | + | NR | + | NR | NR |
| Megakaryocyte Augmentation | + | + | − | + | + | NR |
| T-Cell Proliferation | NR | NR | NR | + | NR | NR |
| Keratinocyte Proliferation | NR | NR | NR | + | NR | NR |
| B-Cell Proliferation/Stimulation | NR | NR | NR | + | + | NR |
| Binding to Human Placental Cell Receptor | + | + | − | − | NR | NR |
| Hemopoietic Proliferation (Normal) | NR | NR | NR | + | + | NR |
| Neuron Augmentation | NR | NR | NR | NR | NR | + |

"+" = activity;
"−" = no activity;
and "NR" = not reported.

As shown in the foregoing table, the six cytokines exhibit different activities. For example, OSM and IL-6 inhibit the growth of melanoma cells; LIF and G-CSF do not. However, LIF, IL-6 and IL-11 and G-CSF differ in that LIF, IL-6 and IL-11 are capable of stimulating proliferation and differentiation of megakaryocytes. OSM binds to human placental cell receptor; IL-6 does not; CNTF, IL-6, OSM and LIF stimulate neuronal differentiation, G-CSF may not.

Although some cytokines may enhance immune system health and white blood cell replacement in patients with depleted lymphocyte populations (e.g., patients undergoing radiation or chemotherapy) or exhibit other desireable biological activity, each cytokine discussed above has a structure unique for intended function(s). Biological mechanisms are known to be highly selective and responsive only when intricate signaling systems invoke particular biochemical responses at a cellular (biochemical) level. Thus, each cytokine targets a specific cell receptor, inducing a particular biological reaction, producing a specific biological result.

These cytokines, CNTF, G-CSF, IL-6, IL-11, LIF and OSM, utilize specific mechanisms for effecting identified cellular responses. Their structural and biochemical specificity do not suggest that alternative cytokines, radically different from these cytokines, would have unexpected advantages in selective biological mechanisms over a much broader range of biological activities. One attempt to provide a therapeutic compound with multiple cytokine function resulted in a fusion protein, PIXY321, having an entire granulocyte macrophage colony stimulating factor (GM-CSF) cytokine, a linking sequence and an entire interleukin-3 (IL-3) cytokine. The extremely large polypeptide (spanning more than two cytokines) has both GM-CSF and IL-3 activity yet is difficult to produce and administer.

SUMMARY OF THE INVENTION

The invention provides a group of therapeutic hybrid cytokines, having a size ranging from about 10 to about 30 kDa, which comprise portions of cytokines: leukemia inhibitory factor (LIF), granulocyte-colony stimulating factor (G-CSF), interleukin-6 (IL-6), interleukin-11 (IL-11), oncostatin-M (OSM), and ciliary neurotrophic factor (CNTF).

IL-6, G-CSF, LIF, IL-11, CNTF and OSM each comprise four α-helical sequences. In each cytokine, the four α-helical sequences are linked by non-α-helical "linking" sequences of about 5–100 amino acids, and in some cases the α-helices are maintained in the proper conformation and geometry with respect to each other through disulfide bridges.

The inventive hybrid cytokines comprise three or four α-helical sequences selected from α-helical sequences of IL-6, G-CSF, LIF, IL-11, CNTF and OSM and linking sequences, ranging from about 5–40 amino acids in length, selected from the linking sequences of IL-6, G-CSF, LIF, IL-11, CNTF and OSM or other desirable linking sequences. In the hybrid cytokines, at least one α-helical sequence is derived from a different cytokine than at least one other α-helical sequence; or, at least one linking sequence of a cytokine differentiates the inventive hybrid cytokine from a corresponding cytokine. In hybrid cytokines having three α-helical sequences selected from the group of cytokines listed, a possible fourth sequence may not correspond to any α-helical sequence in any of the cytokines. Thus, not all hybrid α-helical or linking sequences must derive from the same cytokine α-helical and linking sequences.

As referred to herein, cytokine refers to the amino acid or a DNA sequence encoding the cytokine amino acid sequence of human G-CSF, LIF, IL-6, OSM, CNTF or IL-11, which have been published. DNA sequences and corresponding amino acid sequences are shown in SEQ ID NO:1, SEQ ID NO:2, SEQ ID NO:3, SEQ ID NO:4, SEQ ID NO:5 and SEQ ID NO:6, respectively. Each sequence listing illustrates α-helical and linking sequences for each corresponding cytokine.

Preferably, hybrid cytokine α-helical sequences are selected from corresponding α-helical sequences in the cytokine. "Corresponding" means that a first α-helical sequence of the hybrid cytokine corresponds to a first α-helical sequence from any cytokine, a second α-helical sequence of the hybrid cytokine corresponds to a second α-helical sequence from any cytokine, and a third α-helical sequence and possibly, but not necessarily, a fourth α-helical sequence of the hybrid cytokines correspond to third and fourth α-helical sequences, respectively, from any cytokine.

Inventive hybrid cytokines also contain linking sequences connecting α-helical sequences. The linking amino acid sequences preferably range from about 5 to 40 amino acids and are selected from the linking sequences of each cytokine. The linking amino acids are derived from linking sequences of the group of cytokines. Linking sequences are amino acid sequences (and DNA sequences encoding such amino acid sequences) which facilitate modification and assembly of nucleotide sequences used to express the hybrid cytokines and may, preferably, include amino acid sequences corresponding to nucleotide sequences having a resstriction site, for which restriction enzymes are available.

A linking sequence preferably may be selected from a corresponding linking sequence in a cytokine. Again, "corresponding" means that a first hybrid linking sequence corresponds to a first linking sequence from a cytokine and a second hybrid linking sequence corresponds to a second linking sequence from any cytokine, and so on. Hybrid cytokines may include linking sequences not present in a cytokine, but which contain a restriction site to facilitate assembly of the DNA sequence encoding a hybrid cytokine.

The invention further provides: nucleotide sequences (and degenerate nucleotide sequences) encoding any inventive hybrid cytokine; expression systems capable of expressing the nucleotide sequences into hybrid cytokines; host cells transformed with these expression systems; and methods for recombinantly producing hybrid cytokines, in addition to, pharmaceutical compositions comprising the inventive hybrid cytokines and pharmaceutically acceptable excipients and/or carriers.

DETAILED DESCRIPTION OF PREFERRED EMBODIMENTS

Names of hybrid cytokines are governed by the following conventions: Each hybrid cytokine name may have no less than three characters (a hybrid cytokine name may have more than three characters, depending on the number of α-helical sequences and the particular linking sequences present in the hybrid). In each name, G represents G-CSF; L represents LIF; I represents IL-6; O represents OSM, E represents IL-11 and C represents CNTF. Upper case letters designate α-helical sequences. Lower case letters (whether Arabic numerals, alphabetic or symbolic) immediately following a series of uppercase characters indicate a specific linking sequence. Hybrid cytokine names may include an integer (from 1 to 4) following each uppercase character representing a first, second, third or fourth cytokine α-helical sequence. This trailing integer indicates the location of the α-helical sequence in the originating cytokine. If the location of the α-helical sequence in the hybrid cytokine originates from the same position in a cytokine (i.e., first, second, third or fourth), the character identifying the respective sequence will not have an integer following it.

Thus, for example, a hybrid cytokine having hybrid α-helical sequences I and IV corresponding to α-helical sequences I and IV of G-CSF, hybrid α-helical sequences II and III corresponding to α-helical sequences II and III of IL-11 and hybrid linking sequences I/II, II/III and III/IV, corresponding to linking sequences in G-CSF, IL-11 and G-CSF, respectively, would have a representative name: GEEGϵ. No integers follow any sequence character because each α-helical sequence corresponds to an α-helical sequence in a cytokine. The ϵ symbolic following uppercase letters specifying a hybrid α-helical sequence indicates a unique linking sequence in the hybrid cytokine. Because different linking sequences may occur in hybrid cytokines having identical α-helical sequences, lower-case characters following uppercase characters (and possibly integers) uniquely identify a particular linking sequence. A hybrid cytokine represented by the name C4C3EXβ would have the following sequence origins. Hybrid α-helical sequences I and II originate from the fourth and third α-helical sequences of CNTF, respectively. The third hybrid α-helical sequence corresponds to the third α-helical sequence of IL-11. The fourth hybrid α-helical sequence is represented with an "X," indicating that this α-helical sequence does not originate from any cytokine, G-CSF, LIF, IL-6, IL-11, OSM or CNTF. The symbol β indicates a specific linking sequence for this hybrid cytokine. For example, β may represent that linking sequences I/II and II/III originate from the fourth and third linking sequences of CNTF, respectively, and that a third hybrid linking sequence (III/IV) does not have an origin from any cytokine.

Inventive hybrid cytokines comprise portions of cytokines: leukemia inhibitory factor (LIF), granulocyte-colony stimulating factor (G-CSF), interleukin-6 (IL-6), interleukin-11 (IL-11), oncostatin-M (OSM), and ciliary neurotrophic factor (CNTF).

Preferably, the inventive hybrid cytokines comprise three to four α-helical sequences selected from α-helical sequences of IL-6, G-CSF, LIF, IL-11, CNTF and OSM. In the hybrid cytokine, at least one α-helical sequence is derived from a different cytokine than at least one other α-helical sequence. In hybrid cytokines having three α-helical sequences selected from the group of cytokines listed, a possible fourth sequence may not correspond to any α-helical sequence in any of the cytokines. Thus, not all α-helical sequences must derive from a cytokine α-helical sequence.

Preferably, hybrid cytokine α-helical sequences are selected from corresponding α-helical sequences in the cytokine. Each α-helical sequence may be interrupted by one or more non-helical sequences comprising from 8–30 amino acids.

Exemplary amino acid sequences for human cytokines are represented below in Sequence ID NOS:1–6. The hybrid cytokines of the invention derive amino acid sequences from at least two of the related factors—leukemia inhibitory factor (LIF), granulocyte-colony stimulating factor (G-CSF), interleukin-6 (IL-6), interleukin-11 (IL-11), ciliary neurotrophic factor (CNTF) and oncostatin-M (OSM). The amino acid sequences of each cytokine in human and some other species is known. The encoding genes have been cloned and reported in the literature. Human and murine genes encoding LIF are reported by Moreau et al., *Nature* (1988) 336:690–692 and Simpson et al., *Eur. J. Biochem.* (1988) 175:541–547. Nagata et al., *EMBO J.* (1986) 5:575–581 and Tsuchiya et al., *Proc. Natl. Acad. Sci. USA* (1986) 83:7633–7637, report human and murine G-CSF. Yasukawa et al., *EMBO J.* (1987) 6:2939–2945 and Tanabe et al., *J. Immunol.* (1988) 141:3875–3881 report human and murine IL-6. Malik et al., *Mol. Cell Biol.* (1989)

9:2847–2853 disclose sequences for human OSM and Bruce et al., *Prog. Gr. Fac. Res.* (1992) 4:157–170 discuss encoding sequence genes for simian OSM. Lam et al. *Gene* (1991) 102:271–276 report human CNTF; Stockli et al., *Nature* (1989) 342:920–923 disclose rat CNTF; McKinley et al., *Genomics* (1992) 13:814–819 discuss human IL-11; and Paul et al., *PNAS* (1990) 87:7512–7516 report simian IL-11.

Alignments for the amino acid sequences of cytokines LIF, OSM, G-CSF, IL-6, IL-11 and CNTF, based on their predicted secondary structures, were conducted using a number of software packages including PatMat software (Henikoff et al., *Methods Enzymol.* (1990) 183:111–132); GenPro software (Riverside Scientific, Seattle, Wash.); P/C Gene software (Intelligenetics, Inc., Mountain View, Calif.); Scor Edit (J. Durand, Seattle, Wash.); Motif Program (Smith, *Proc. Natl. Acad. Sci. USA* (1990) 87:826–830), as implemented in the Protomat/Motif J software (Henikoff, Seattle, Wash.); and MacDNASIS software (Hitachi Software Engineering America, Ltd., San Bruno, Calif.).

Application and interpretation of these programs resulted in predicted secondary structures for the amino acid sequences of cytokines which comprise components of the inventive hybrid cytokines.

Figure 1:
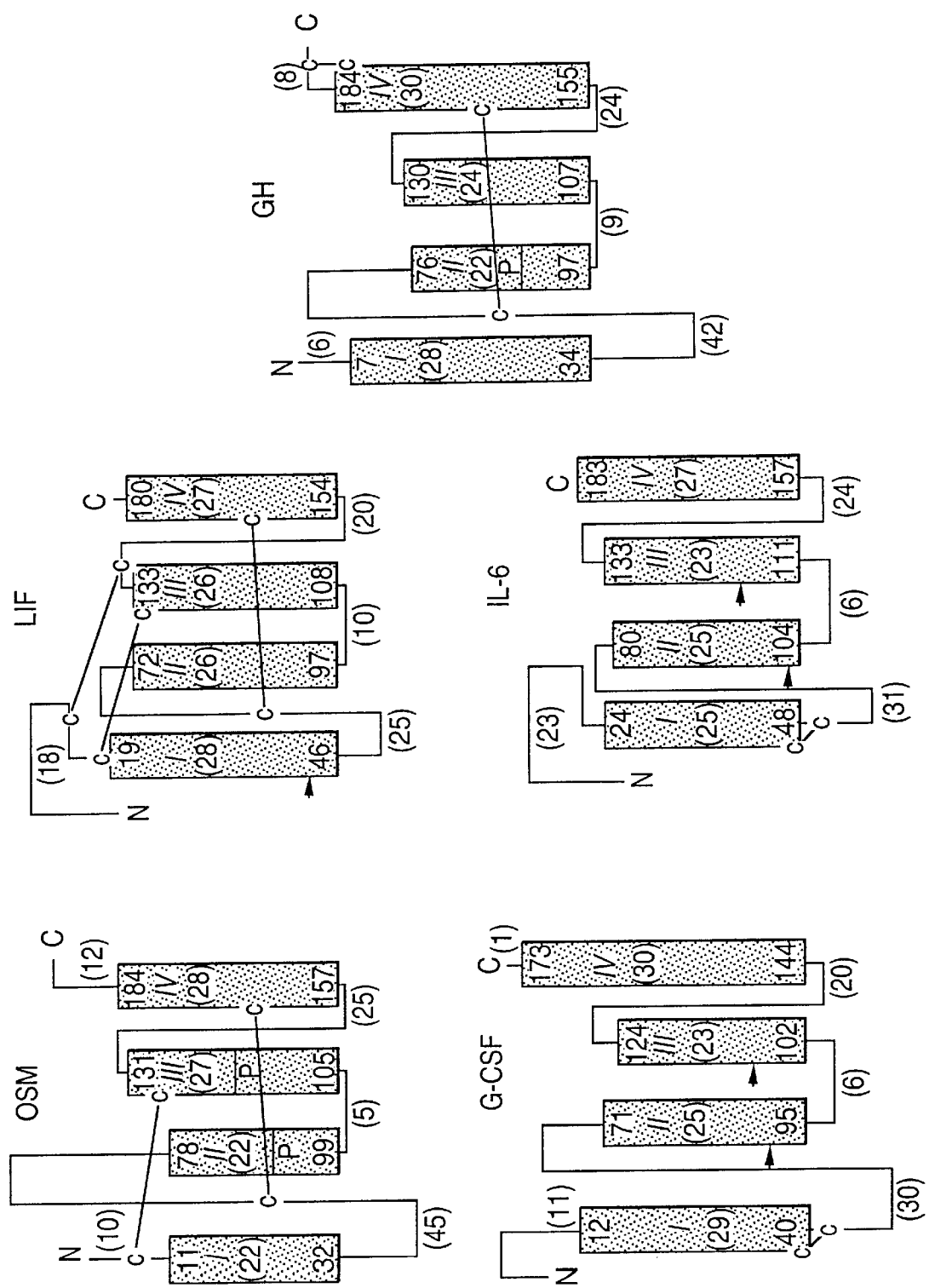
FIG. 1 shows the organization of the four α-helical sequences deduced for the OSM, LIF, G-CSF and IL-6 cytokines. Also shown in this figure is an α-helical sequence organization for growth hormone which has been confirmed by X-ray crystallography.

The results of this work are shown in FIG. 1. As shown in FIG. 1, each of LIF, G-CSF, IL-6, and OSM contain four α-helical sequences, numbered I–IV. The schematics also illustrate disulfide bridges; OSM and LIF having similar disulfide bridge locations. As shown, OSM and G-CSF have similar structures with LIF and IL-6, respectively. The disulfide bond linking a fourth α-helical sequence and a linking sequence between the first and second α-helical sequences determined in LIF and OSM is similarly found in the structure of growth hormone.

In human OSM, the α-helical sequence I extends approximately from amino acid residue 11–32; α-helical sequence II from residue 78–99; α-helical sequence III from residue 105–131; and α-helical sequence IV from residue 157–184. The locations of the various sequences of α-helices for human forms of cytokines are shown in Table II, wherein the start or end of an α-helical sequence listed below.

TABLE II

| CYTOKINE | α-HELICAL SEQUENCE (amino acid residue #) | | | |
|---|---|---|---|---|
| | I | II | III | IV |
| OSM | 11–32 | 78–99 | 105–131 | 157–184 |
| LIF | 19–46 | 72–97 | 108–133 | 154–180 |
| G–CSF | 11–41 | 71–95 | 102–124 | 144–173 |
| IL–6 | 24–48 | 80–104 | 111–133 | 157–183 |
| IL–11 | 18–40 | 54–93 | 103–131 | 150–175 |
| CNTF | 16–44 | 62–98 | 102–134 | 151–181 |

As implied in the table, various α-helical sequences in each case will be linked by non-helical amino acid sequences, designated herein "linking sequences." Amino acid linking sequences preferably range from about 5 to 40 amino acids. Linking sequences are derived from linking sequences of cytokines or are spliced to insert a restriction site to facilitate assembly of the hybrid cytokine. Linking sequences are designed to functionally and sterically space apart and properly orient α-helical regions of the resulting hybrid cytokines. A linking sequence may be selected from a corresponding linking sequence in a cytokine. Thus, a linking sequence I/II in the hybrid may be derived from linking sequence I/II of one of the G-CSF, OSM, LIF, IL-6, IL-11 and CNTF. Hybrid cytokines may include linking sequences not precisely present in a cytokine. Linking sequences themselves may be hybrids of linking sequences from two or more cytokines. For example, a portion of a linking sequence which trails a first α-helical sequence of IL-6 may combine with a portion of a linking sequence leading a second α-helical sequence of G-CSF, the trailing portion and leading linking sequences joined by a hybrid sequence which includes a restriction site to facilitate assembly of the hybrid cytokine. Graphically represented, a hybrid cytokine would appear, in relevant part, as:

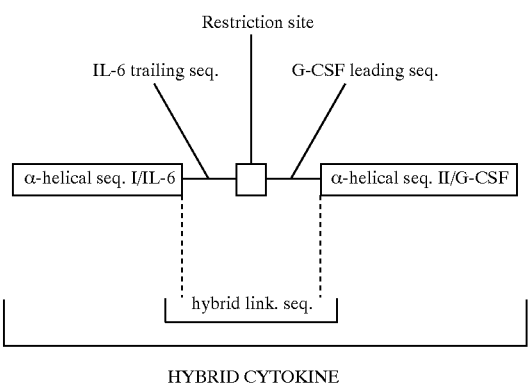

HYBRID CYTOKINE

Linking sequence I/II in OSM, for example, extends from residue 33–77; linking sequence II/III from position 100–104; and linking sequence III/IV from position 132–156. Locations of various sequences of linking sequences for human forms of six cytokines are shown in Table III, wherein the start or end of a linking sequence may vary by as many as five amino acids from the consensus start and end of linking sequences listed below. Linking sequence I/II corresponds to an amino acid sequence between α-helical sequences I and II; linking sequence II/III, between α-helical sequences II and III; and linking sequence III/IV, between α-helical sequences III and IV.

TABLE III

| CYTOKINE | LINKING SEQUENCES (amino acid residue #) | | |
|---|---|---|---|
| | I/II | II/III | III/IV |
| OSM | 33–77 | 100–104 | 132–156 |
| LIF | 47–71 | 98–107 | 134–153 |
| G–CSF | 42–70 | 96–101 | 125–143 |
| IL–6 | 49–79 | 105–110 | 134–156 |
| IL–11 | 42–53 | 94–102 | 132–149 |
| CNTF | 45–61 | 99–101 | 135–150 |

A hybrid cytokine polypeptide comprises a first, second, third and preferably a fourth α-helical sequence. Each α-helical sequence is derived from an α-helical sequence of cytokines LIF, G-CSF, IL-6, IL-11, OSM or CNTF, preferably a corresponding α-helical sequence. Therefore in inventive hybrid cytokines, at least one of these three or four α-helical sequences is derived from a different cytokine.

Preferred inventive hybrid cytokines have α-helical sequences derived from cytokines of the species intended for use. For human therapy, all four α-helical sequences are derived from human forms of cytokines (preferably, the inventive hybrid cytokines comprise human α-helical and linking sequences). For veterinary use, for example bovine, all α-helical sequences are derived from bovine cytokine sequences.

Preferred hybrid cytokines have either α-helical sequences I, II, and III from the same cytokine and IV from a different cytokine, or conversely, sequences II, III and IV are from the same cytokine and sequence I is from a different one. In general, it is preferred that hybrid sequences II and III originate from the same cytokine.

Of particular significance: in all six cytokines, α-helical sequences I and IV have opposite N→C orientations. Similarly, α-helical sequences II and III have opposite polarity N→C orientations. In more preferred hybrid cytokines, relative polarity orientation of hybrid sequences I–IV maintains a natural pattern, in particular, hybrid sequences I and IV, with respect to each other.

In OSM and LIF, length of linking sequence I/II and linking sequence III/IV permit sequences I and IV to have the same N→C orientation as sequences II and III, respectively. Similarly, in G-CSF and IL-6, α-helical sequences I and II and III and IV to have parallel N→C orientations. However, a "double negative" for G-CSF and IL-6 results in the same relative sequence I and IV orientations in G-CSF and IL-6, as is the case in OSM and LIF.

Thus, preferred hybrid cytokines have both linking sequences I/III and III/IV longer (about 20–30 amino acids), permitting parallel orientation of joined helical sequences as in LIF and OSM. Linking sequences may be selected so as to assure anti-parallel orientation of α-helical sequences I and IV in all cases.

Particularly preferred hybrid cytokines comprise: 11) first and fourth α-helical sequences derived from the same cytokine, 2) second and third α-helical sequences derived from the same cytokine; 3) at least one sequence derived from IL-6; or 4) with respect to α-helical sequence origins, have α-helical sequences I–IV as represented below. GGGI; OOOI ; LLLI; IIIO; GGGO; OOOG; LLLO; IIIG; GGGL; OOOL; LLLG; IIIL; IGGG; IOOO; ILLL; OIII; OGGG; GOOO; OLLL; GIII; LGGG; LOOO; GLLL; LIII; GLLG; GIIG; IGGI; LOGI; LLII; LLGG; IIGG; EGGG; OOOE; LLLE; IIIE; LEEE; CEEE; ECCC; EEEC; GCCC; CCCE; LLLC; OOOC; IIIC; GCCG; CGGC; LCCC; CCLL; CCII; CGGG; CELI; and ECCE.

And, especially preferred hybrid cytokines include, but are not limited to: GGLL; GGII; GGOO; GGGI; IGGG; GILO; LOGI; LLII; GGGO; GGGL; OOOG; LLLG; GOOO; OGGG; LGGG; GGGI.

In each preferred hybrid cytokines, each hybrid α-helical sequence has a corresponding sequence in a cytokine, therefore, no integers show position origin. The α-helical sequences shown are linked through non-helical linking sequences of 5–40 amino acids. Preferred hybrid cytokines have linking sequences derived, even if only partially, from corresponding linking sequences of cytokines. However, other preferred hybrid cytokines may or may not have linking sequences derived from corresponding cytokines. These preferred hybrid cytokines may alternatively have linking sequences selected to maintain a hybrid three-dimensional, α-helical sequence conformation similar to the originating cytokines. In the hybrid cytokines previously shown, linking sequences may preferably be derived from corresponding linking sequences of a cytokine. Thus, for example, a linking sequence between α-helical sequence I and II is derived from the linking sequence I/II of the same cytokine:

Because disulfide linkages, as shown in FIG. 1, are thought to contribute to maintaining conformation, preferred suitable linking or α-helical sequences provide at least two cysteine residues, furnishing appropriate disulfide links.

Hybrid Cytokine Synthesis

Inventive, hybrid cytokines may be made using known solid-phase peptide synthesis techniques combined with linking technology. However, synthesis of appropriate-length peptides is laborious and may be difficult. Subsequent to peptide synthesis, proper conditions are required to effect three-dimensional folding of synthesized peptides to assume α-helical and tertiary conformations discussed above. Alternatively, inventive hybrid cytokines may be prepared using recombinant DNA techniques.

Recombinant DNA technology for producing desired proteins is known by ordinarily skilled artisans, including provision of a coding sequence for a desired protein, the coding sequence operably linked to DNA sequences capable of effecting its expression. It may be desirable to produce the hybrid cytokines as fusion proteins, freed from upstream, downstream or intermediate sequences, or as proteins linked to leader sequences, effecting secretion of desired cytokines into cell culture medium.

A DNA-based expression system will also contain "control sequences" necessary for transcription and translation of a message. Known, required expression components, include constitutive or inducible promoter systems, translational initiation signals (in eucaryotic expression), polyadenylation translation termination sites, and transcription terminating sequences. Host vectors containing controls which permit operable linking of desired coding sequences to required control systems are known by artisans ordinarily skilled in recombinant technology. Such vectors can be found which are operable in a variety of hosts. High stringency, as used herein, means the integrity of the originating double-helix DNA structure is maintained in the recombinant DNA.

Inventive hybrid cytokines may be produced in procaryotic cells using appropriate controls, such as trp or lac promoters, or in eucaryotic host cells, capable of effecting post-translational processing that permits proteins to assume desired three-dimensional conformation. Eucaryotic control systems and host vectors are known; including the leu and glycolytic promoters useful in yeast, the viral SV40 and adenovirus and CMV promoters in mammalian cells, inducible promoters such as the metallothionein promoter also suitable for mammalian cells, and the baculovirus system which is operable in insect cells. Plant vectors with suitable promoters, such as the nos promoter have also been used successfully.

Hybrid cytokines may be prepared in procaryotic as well as eucaryotic hosts. Although generally glycosylated in their native forms, glycosylation is known not to be essential for an activity of any of the foregoing six cytokines. Suitable refolding conditions, as understood by ordinarily skilled artisans, may provide alternative techniques for obtaining a desired conformation.

Standard laboratory manuals (e.g., Sambrook et al. published by Cold Spring Harbor Laboratories, Cold Spring Harbor, N.Y.), present standard techniques and methodologies for expressing DNAs encoding a desired protein, culturing appropriate cells, providing suitable expression conditions, and recovering a resulting protein from culture. In preparing the inventive hybrid cytokines, a suitable DNA encoding the desired hybrid, constructed utilizing any of the foregoing techniques, is operably linked to control sequences in a suitable expression system which is then transformed or transfected into a compatible host. Host cells are cultured using conditions appropriate for growth, expression of the desired hybrid cytokine being preferably induced after some predetermined growth level has occurred. Hybrid cytokine production is monitored and the desired hybrid collected from culture either from a supernatant or by first lysing host cells with an appropriate agent.

Procedures analogous to those employed for purifying cytokines may be used to purify the isolated hybrid cytokine for use in therapeutic or diagnostic compositions.

Preparation of Antibodies

Antibodies specifically reactive with the hybrid cytokines of the invention or immunoreactive fragments of these antibodies may be prepared using standard immunization protocols. These may be utilized as polyclonal antisera or the spleen cells or peripheral blood lymphocytes of the immunized animals may be immortalized to obtain isolated cell cultures which produce monoclonal antibodies specific for these hybrids. The antibodies may be used intact, or as fragments such as Fab, Fab' or F(ab')2 fragments. As the hybrid cytokines are relatively large proteins, it should not be necessary to enhance their immunogenicity by conjugation to carrier; however, such enhancement is possible and construction of such conjugates is well known in the art.

Thus, the hybrid cytokine, optionally conjugated to an immunological carrier, is administered in a standard immunization protocol with or without the use of adjuvant to a suitable subject, usually rats, sheep, or rabbits. Antibody formation is monitored by titrating the serum using the cytokine as antigen and employing standard immunoassay techniques. When high titers are achieved, the sera can be used per se or the spleen cells or peripheral blood lymphocytes isolated and immortalized, for example, using the fusion technique of Kohler and Millstein to provide immortalized cells capable of secreting the desired monoclonal antibodies. Individual clones of these immortalized cells are then screened, again using standard immunological techniques, for those colonies which secrete antibodies specifically immunoreactive with the hybrid cytokine immunogen.

The antibodies prepared in the foregoing manner or fragments thereof are useful in diagnostic assays for monitoring the pharmacokinetics and progress of therapeutic regimens using the hybrid cytokines of the invention. Thus, the dosage levels of the hybrid cytokines in the therapeutic applications set forth below can be regulated according to the metabolic fate of the previously administered dosages.

Administration and Utility

The invention further provides: nucleotide sequences encoding any inventive hybrid cytokine; expression systems capable of expressing the corresponding nucleotide sequences; host cells transformed with these expression systems; and methods for recombinantly producing hybrid cytokines. The invention permits pharmaceutical compositions comprising the inventive hybrid cytokines, polypeptides and/or pharmaceutically acceptable excipients and/or carriers. The invention permits antibodies or fragments specifically immunoreactive with these hybrid cytokines.

The hybrid cytokines of the invention are useful in treating the indications for which their native counterparts are often employed. However, the hybrid forms of the cytokines possess unique properties which make them suitable alternatives in the methods and procedures commonly employed with respect to the native molecules. For example, a hybrid cytokine composed of α-helical sequences from two different cytokines may have biological activity of both cytokines.

In addition, some of the hybrid cytokines are capable of binding the receptors ordinarily bound by the native molecules but fail to activate these receptors. These forms of the hybrid cytokines are, thus, antagonists. These may be useful in treating conditions where presence of the cytokine that ordinarily binds to the receptor is responsible for undesired cell proliferation. For example, IL-6 and OSM are known to be present in high levels with Kaposi's sarcoma. These are found also in high concentrations in the synovial fluid from patients suffering from rheumatoid arthritis. In these conditions, the hybrid cytokine antagonists are particularly useful.

Conversely, the hybrid cytokines which are agonists can be employed in circumstances wherein the cytokines are often used. For instance, these agonist hybrid cytokines may be used in liver cell regeneration and in in vitro fertilization procedures to enhance these processes.

The hybrid cytokine may possess properties exhibited by neither of its components taken alone. It is known, for example, that co-administration of LIF and G-CSF results in a synergistic effect in inhibiting colony formation and inducing differentiation of human U937 and HL60 myelocytic leukemia cell lines although neither alone has this effect (Maekawa et al., *Leukemia* (1989) 3:270–276. ) Similarly, we have found that although neither LIF nor OSM inhibit colony formation of U937, when supplied in combination, at 10 ng/ml using 300 cells in soft agar, more than 60% inhibition of colony formation is obtained.

Thus, combination of the α-helical sequences from more than one growth factor results in hybrid cytokines with a unique spectrum of properties. These inventive hybrid cytokines are useful generally in inhibiting tumor proliferation, in bone remodeling, in stimulating the growth of desired cells, such as neurites or T-cells, and in enhancing the differentiation of hematopoietic cells. Hybrid cytokines are therefore highly useful in direct treatment of malignancies. The inventive hybrid cytokines are especially useful in maintaining the general health and immune capacity of a subject undergoing cytoreductive therapy (radiation therapy or chemotherapy) for such indications.

The selection of particular conditions or procedures suitable for the hybrid cytokine in question depends, of course, on its particular agonist or antagonist activity spectrum.

The properties of a particular hybrid can be ascertained through standard in vitro tests known in the art. Such tests include those, for example, which show: 11) induction of differentiation into macrophages (Tomita et al., *J. Biol. Chem.* (1984) 259:10978–10982); 2) enhancement of interleukin-3-dependent colony formation of primitive blast cells (Leary et al., *Blood* (1990) 75:1960–1964); 3) promotion of megakaryocyte growth and differentiation (Metcalf et al., *Blood* (1990) 76:50–56); 4) induction of neuronal differentiation (Yamamuri et al., *Science* (1989) 246:1412–1416); and 5) induction of bone resorption (Ishimi et al., *J. Immunol.* (1990) 145:3297–3303). A large number of in vitro assays indicating an ability of cytokines to stimulate growth and differentiation of desired cells and inhibit the growth of undesired malignant cells is known in art. Animal model systems can also be used to verify unique, unexpected spectrum of properties associated with each hybrid cytokine.

Particularly useful in vitro tests which can be used to confirm the spectrum of activity of the hybrid cytokines include, but are not limited to the: 1) inhibition of DNA synthesis in M-1 myeloid leukemic cells; effect on growth of human A-375 melanoma cells (Zarling et al., *Proc. Natl. Acad. Sci. USA* (1986) 83:9739–9743); or effect of these cytokines on embryonic stem cells cultured in vitro (Smith et al., *Devel. Biol.* (1987) 121:1–9 and Williams et al., *Nature* (1988) 336:684–687).

The foregoing procedures can be adapted to assess both agonist and antagonist behavior. In assessing antagonist behavior, a hybrid cytokine may be used in the presence of a known agonist and its effect on the activity of the known agonist is assessed.

As set forth above, the hybrid cytokines of the invention are applicable to in vivo and in vitro procedures involving both human and animal cells. They are suitable for both medical and veterinary use.

For therapeutic use, the hybrid cytokines of the invention are formulated into standard pharmaceutical compositions suitable for the administration of proteins. Suitable formulations can be found, for example, in Remington's Pharmaceutical Sciences, latest edition, Mack Publishing Company, Easton, Pa. Comparable compositions for veterinary use are also known in the art. Generally, administration is systemic, usually by injection, such as intravenous or intramuscular injection or can be effected by transdermal or preferably transmucosal delivery. Suitable formulations for effecting transmucosal delivery include, for example, various detergents and bile salts or fusidic acid derivatives.

The dosage levels of the hybrid cytokines of the invention are comparable to those useful for the native molecules. These levels are understood in the art, and the precise dosage can be adjusted according to the condition of the patient, the mode of administration, and the judgment of the attending physician.

The hybrid cytokines of the invention may also be labeled using suitable fluorometric, colorimetric, enzymic, or radioactive labels for use in assays to ascertain the formation of antibodies in patients being treated. Nucleotide base and amino acid sequence listings for cytokines and inventive hybrid cytokines appear below. The invention, illustrated by the following examples, should not be deemed as limited in any way by these representative examples.

EXAMPLE 1 cDNA clones for the human cytokines G-CSF and IL-6 were obtained by PCR amplification (Kawasaki, PCR Protocols, A Guide to Methods and Applications, pp. 21–27 Academic Press, 1990) using primers based upon published sequences. The sequence of the cDNA encoding the mature protein of each cytokine was joined to synthetic DNA fragments encoding the signal peptide sequence derived from E. coli alkaline phosphatase and the FLAG® octapeptide sequence (Hopp et al., BioTechnology (1988) 6:1204–1210). The resulting fragment, with a unique Kpn I site and BamH I site at its 5'end and 3'end, respectively, was inserted between the Kpn I and BamH I sites, within the multiple cloning site of the mammalian expression vector pBL3. pBL3 was derived from mammalian episomal expression vectors pMEP4 and pCEP4 (Invitrogen Corp.). Specifically, a 600 bp Spe I—Kpn I fragment spanning the CMV promoter from pCEP4 and a 9500 bp Xba I—Kpn I vector fragment from pMEP4 were isolated and ligated together to form pBL3.

Using the IL-6 and G-CSF cDNA sequences prepared and obtained as described above, a hybrid cytokine, IGGGγ (SEQ ID NO:7, below), was prepared having sequences from both cytokines. An alkaline phosphatase signal sequence for protein secretion extends from amino acid residues –30 to –10. The FLAG® octa-peptide sequence for recombinant protein detection and cleavage extends from amino acids –9 to –3. A Hind III restriction site was positioned between the FLAG® sequence and the start of the hybrid cytokine mature protein sequence. The first 42 amino acids of this hybrid cytokine were derived from human IL-6 and amino acids 43–181 were derived from human G-CSF. The IGGGγ construct was made by fusing the IL-6 and G-CSF cDNA at a precise location in the hinge sequence between helix 1 and helix 2 domains using PCR (PCR Protocols, supra at pp. 177–183).

Plasmid pBL3 was used to express the hybrid cytokine. pBL3 was transfected into 293-EBNA cells (available from Invitrogen Corp.) using cationin lipid DOTAP® according to the manufacturer's procedure (Boerhinger Mannheim). The cell culture media were changed one day after transfection to remove excess DOTAP®. The cell culture media were then collected two days later to obtain the inventive IGGGγ hybrid cytokine for a biological activity assay.

Biological acivity of the hybrid cytokine was based on an assay useful in determining an ability of test samples to support growth of 32D cells, a G-CSF-dependent cell line. Test samples of isolated hybrid cytokines were added to cell culture media at different concentrations and incubated for three days. Biological activity was determined by measuring viability (in %)of the 32D cells using a trypan blue exclusion staining technique. A comparison of the activity of the hybrid cytokine IGGGγ to human G-CSF suggests a % Viability about 5 to 10% of values obtained for G-CSF activity. Table IV reports % Viability assay results for various test samples:

TABLE IV

| Test Samples | % Viability |
| --- | --- |
| RPMI media (neg. control) | 4.0 |
| G-CSF 10 ng/ml | 21.8 |
| G-CSF 25 ng/ml | 34.9 |
| G-CSF 50 ng/ml | 42.0 |
| G-CSF 100 ng/ml | 41.1 |
| Mock transfected DNA control 1.0% | 6.1 |
| Mock transfected DNA control 2.5% | 4.0 |
| Mock transfected DNA control 5.0% | 3.0 |
| Mock transfected DNA control 10.0% | 5.0 |
| IGGGγ 1.0% | 2.0 |
| IGGGγ 2.5% | 8.9 |
| IGGGγ 5.0% | 7.7 |
| IGGGγ 10.0% | 6.2 |

EXAMPLE 2

Hybrid Cytokines LLLI, LLLIα, IIILα, IIIL, IIIG, IGGI (SEQ ID NO:17, SEQ ID NO:18, SEQ ID NO:19 SEQ ID NO:20, SEQ ID NO:21, SEQ ID NO:22 and SEQ ID NO:23, respectively) were made via transient transfection into 293-EBNA cells (mammalian expression system) according to a procedure akin to the procedure described in Example 1.

(IL6.1, LIF.1) and (IL11.3) are plasmids expressing type IL-6, LIF and IL-11 cytokines, respectively. LLLI and LLLIα refer to plasmids expressing hybrid cytokines LLLI and LLLIα, respectively. The first three α-helical sequences of LLLI and LLLIα were derived from LIF and the fourth α-helical sequence was derived from IL-6. LLLIα has two additional amino acids inserted in a linking sequence between α-helices III and IV, as compared with LLLI, which has no additional amino acids at this location. IIILα and IIIL are plasmids expressing hybrid cytokines, having the first three α-helical domains derived from IL-6 and the fourth α-helical domain derived from LIF. IIILα has an additional 2 amino acids inserted in the hinge sequence between α-helices III and IV when compared to IIL. IIIG is a plasmid expressing a hybrid cytokine having the first three α-helical sequences derived from IL-6 and the fourth α-helical sequence from G-CSF. IGGI is to a plasmid expressing a hybrid cytokine with the first and fourth α-helical sequences derived from IL6 and the second and third α-helical sequences derived from G-CSF.

Each transfection was assayed in a 7TD1 assay, an assay based on the capability of the test samples to support the growth of an IL6-dependent cell line, 7TD1, obtained from ATCC (American Type Culture collection), according to the following procedure.

To quantify the significance of the 7TD1 assay results, Western blot analyses of the various tested samples were conducted to determine the degree of expression of the hybrid cytokines as compared with cytokines. An anti-FLAG® antibody was used to measure protein expression of each recombinant polypeptide. Results obtained establish that hybrid cytokine expression levels were much lower than expression levels for IL-6, IL-11 and LIF cytokines. The data presented in FIG. 2, when interpreted in view of lower hybrid cytokine concentrations per unit of culture media tested, support a conclusion that the hybrid cytokines have activities equal to IL-6 or IL-11. The data presented in FIG. 2 should be interpreted accordingly.

Hybrid cytokine test samples were added to a culture media containing 7TD1 cells. The amount of viable 7TD1 cells was determined 72 hours later by staining the cells with a metabolic dye MTS® according to the manufacturer's (Promega) procedure. 7TD1 cells were resuspended in RPMI culture media+10% FBS (fetal bovine serum) and plated in 96-titer plates. An indicator dye (MTS®) was added to the cells 2 to 3 days later. The cells were returned to a $CO_2$ incubator for 1 hour before determining an A490 using the plate reader, which is a colorimetric assay that uses the tetrazolium salt of MTS to report cell proliferation, viability and cytotoxicity. The indicator dye shows cell activity by serving as substrate for mitochrondrial dehydrogenases for the formation of soluble formazan dyes which are quantitated using a plate reader.

Figure 2:
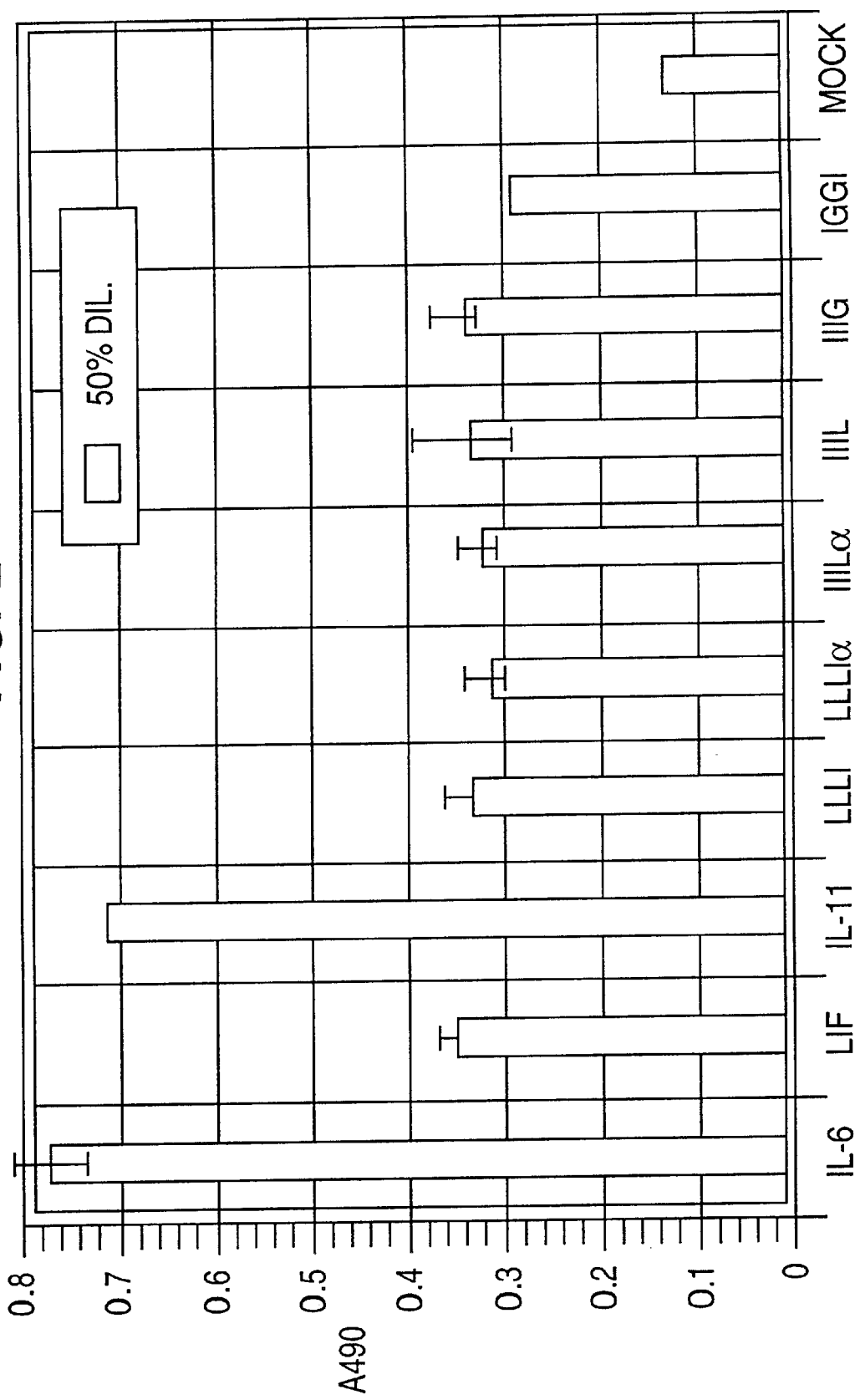
FIG. 2 illustrates biological activity data on 7TD1 cell proliferation for seven hybrid cytokines: LLLI; LLLIα; IIILα; IIIL; IIIG, IGGI, as compared against cytokine and mock assays.

All hybrid cytokine and cytokine test samples stimulated 7TD 1 proliferation, as compared with mock transfected control samples derived from conditioned media of 293-EBNA cells transfected without plasmid DNA. Samples with the highest activity were the ones derived from wild type IL-6 and IL-11. FIG. 2 illustrates activity assay data for seven hybrid cytokines prepared and obtained in this example. Activities of inventive hybrid cytokines are about 40–50% of IL-6, IL-11 and LIF cytokines. In view of a lower degree of hybrid expression in this system, the activities of the hybrids most likely match activities of corresponding cytokines.

EXAMPLE 3

In view of the relatively poor expression of hybrid cytokines in a mammalian cell line, *E. coli* (prokaryotic cells) was used to express hybrid cytokine IGGI. Hybrid cDNA sequences encoding hybrid cytokine amino acid sequences were cloned according to the procedures used in Examples 1 and 2, above. The cDNAs flanked by a HindIII site and a BamHI site between the HindIII and BamHI site of an expression vector pT.His in such way that the cytokine cDNA was expressed under the control of a tac promotor as a fusion protein with methionine followed by 6 histidine residues at the N-terminus. *E. coli*, harboring expression plasmids for IL-11, IGGI and IL-1α, were induced with IPTG. The recombinant hybrid cytokine and cytokine polypeptides were purified from the cell extract using a His.Bind resin (Novagen) according to the manufacturer's procedure.

Figure 3:
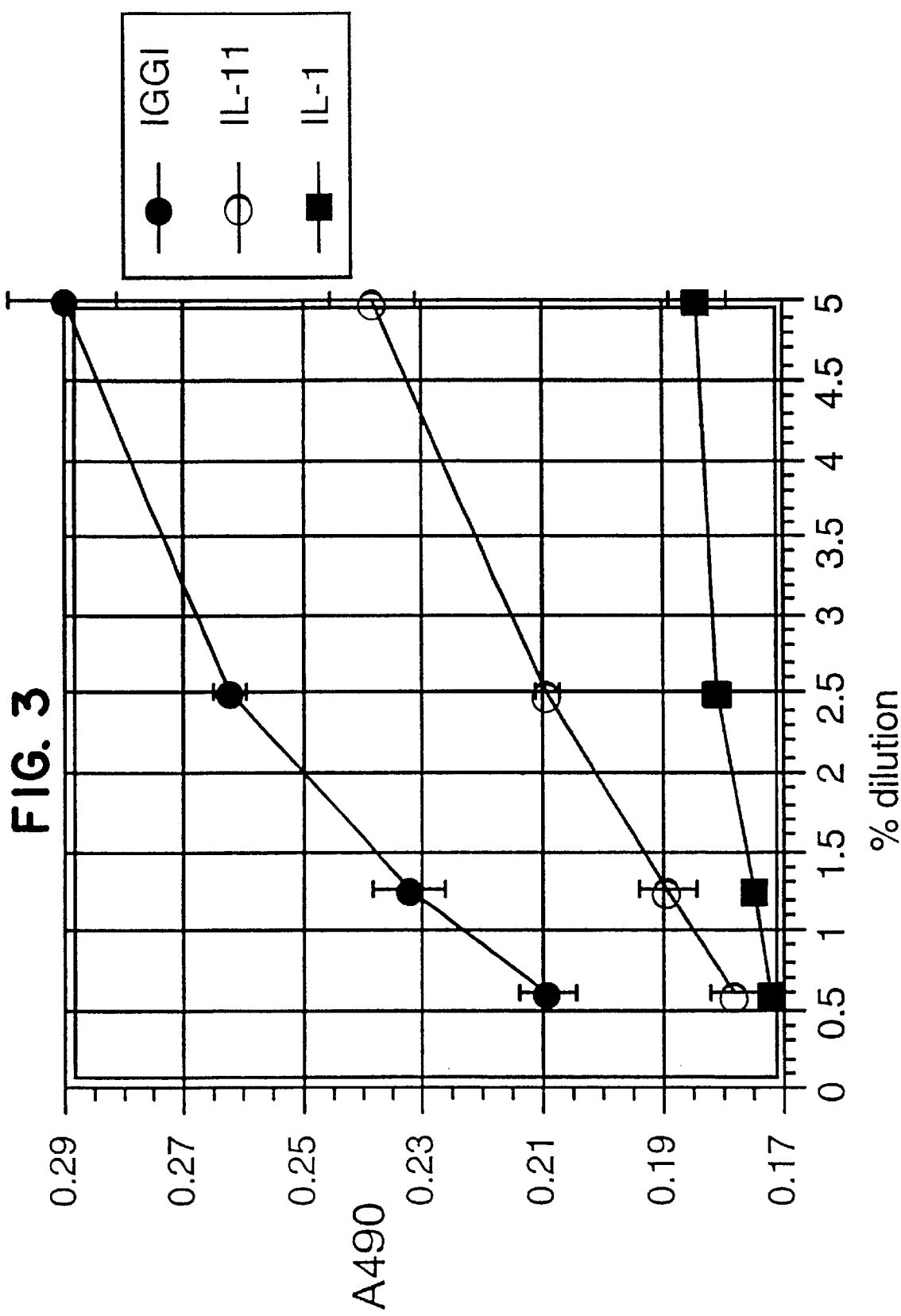
FIG. 3 shows a dose response curve of hybrid cytokine IGGI and cytokines IL-11 and IL-1 on 7TD1 cell proliferation, a measure of IL-6 biological activity.

FIG. 3 shows a dose response curve for *E. coli* produced hybrid cytokine IGGI, IL-11, and IL-1α on 7TD1 proliferation. SDS gel analysis indicates the 3 cytokines tested were expressed at similar levels in *E. coli*. Hybrid cytokine IGGI and cytokine IL-11 have higher activity when compared to IL-1α.

EXAMPLE 4

Using a method as described in the foregoing examples, inventive hybrid cytokines were prepared from cytokines IL-11, G-CSF, LIF and IL-6. Complete amino acid and nucleotide sequences for the cytokines appear below (SEQ ID NO:6, SEQ ID NO:1, SEQ ID NO:2 and SEQ ID NO:3).

Hybrid cytokine LLLE (SEQ ID NO:24), comprises sequences from LIF and IL-11 cytokines. Specifically, the hybrid sequence from 1 to 148 corresponds to a sequence derived from the first three α-helical sequences of LIF, and the hybrid sequence from 149 to 191 corresponds to sequence derived from the fourth α-helical sequence of IL-11. The hybrid cytokine IIIE (SEQ ID NO:25) comprises sequences from IL-6 and IL-11, specifically, the hybrid sequence from 1 to 139 corresponds to a sequence derived from the first three α-helical sequence of IL-6, and the hybrid sequence from 140 to 183 corresponds to a sequence derived from the fourth α-helical sequence of IL-11. In yet another exemplary hybrid cytokine, GGGE (SEQ ID NO:26), the hybrid sequence from 1 to 133 corresponds to a sequence derived from the first three α-helical sequences of G-CSF, and the hybrid sequence from 134 to 177 corresponds to sequence derived from the fourth α-helical sequence of IL-11.

EXAMPLE 5

In this Example, hybrid cytokines, expressed in Examples 4–6 above, were used in assays designed to determine ability of inventive hybrid cytokines to stimulate the formation of cell colonies from mouse bone marrow cell cultures, as compared with cytokines.

In the assay, bone marrow cells, isolated from mouse femur, were cultured in the presence of various conditioned media (with appropriate cells for each respective assay) from Vero E6 cells transfected with expression vectors of various hybrid cytokines. In results shown in Table V, two hybrid cytokines, IIIG and IGGI, increased colony formation units (CFU—defined as the number of cell colonies formed) as compared with a control medium containing untransfected Vero E6 cells. IIIG transfected cells had CFU values nearly equivalent to values obtained for G-CSF transfected cells, prepared and tested in a like manner. This is surprising in view of the fact that only one of four α-helical sequences was derived from G-CSF.

TABLE V

| SAMPLES | CFU.1 | CFU.2 | CFU.3 | CFU.4 | Avg. | St. Dev. |
| --- | --- | --- | --- | --- | --- | --- |
| Control Medium | 55 | 59 | 54 | 55 | 55.8 | 2.2 |
| IIIG | 87 | 77 | 93 | n.a | 85.7 | 8.1 |
| IGGI | 67 | 59 | 63 | 59 | 62 | 3.8 |
| G-CSF | 87 | 87 | 79 | 90 | 88 | 3.6 |

EXAMPLE 6

As in Example 2 above, hybrid cytokines IIILα, LLLIα, GGGE, LLLE, IIIE, IIIL, LLLI, IGGI and IIIG were assayed for proliferation of 7TD1 cells obtained from ATCC.

Figure 4:
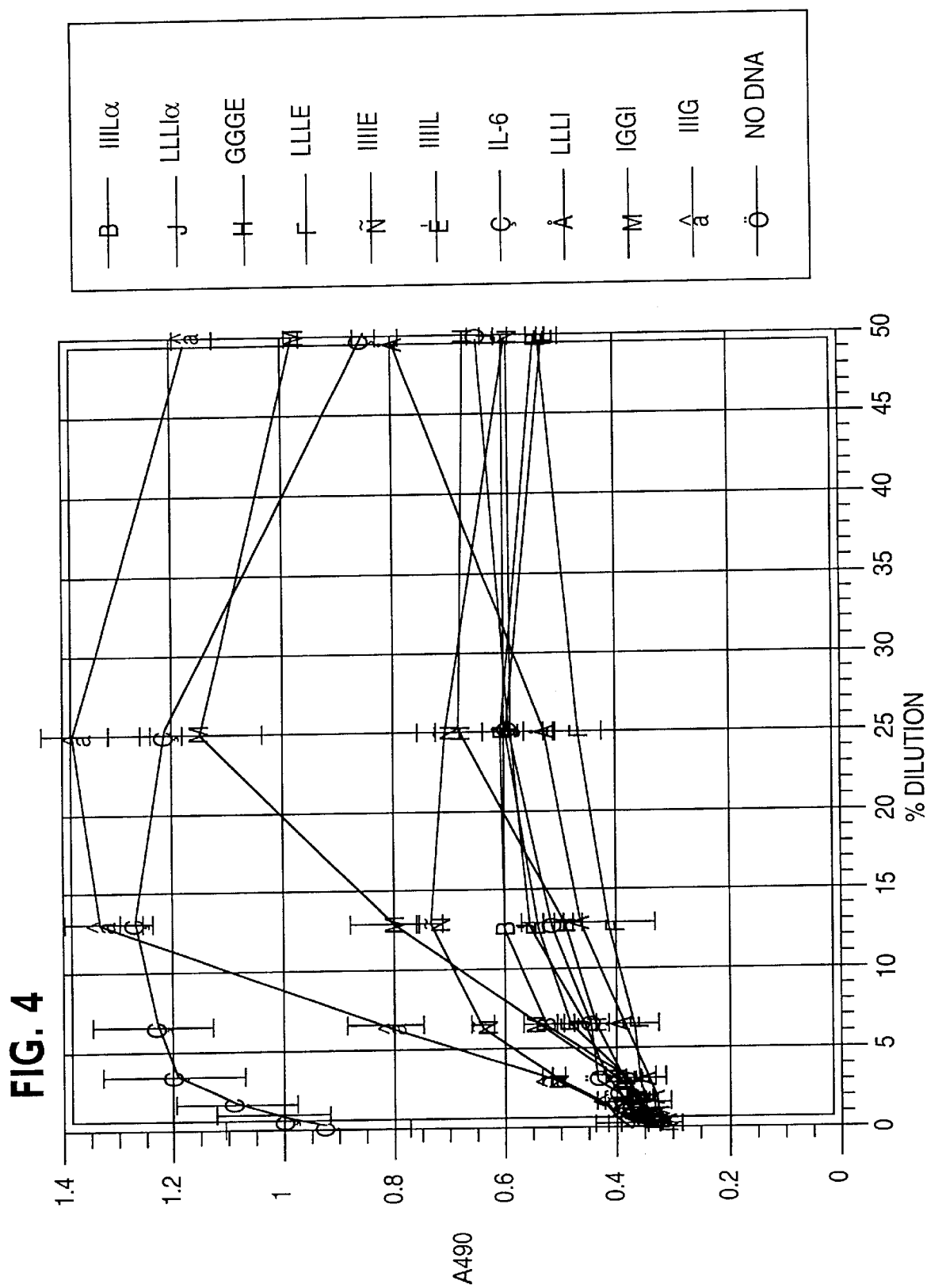
FIG. 4 illustrates biological activity assay of recombinant IL-6 and various inventive hybrid cytokines obtained from culture medium of Vero E6 cells stably transfected with varioius cytokine expression plasmids. Non-transfected culture medium served as a control.

FIG. 4 represents activity assay data of recombinant IL-6 and these various hybrid cytokines made from stablly transfected Vero E6 cells using culture medium from non-transfected cells as a control (no DNA). Culture media from IL-6 and two hybrid cytokines, IIIG and IGGI, transfected cells exhibited mitogenic proliferation activity for 7TD1 cells.

EXAMPLE 7

In a procedure similar to Example 5, hybrid cytokines IIIG and GGGE were prepared and assayed to determine their respective abilities to stimulate formation for CFU-GM from murine bone marrow. Human G-CSF has sufficient sequence homology with a corresponding murine G-CSF cytokine to obtain relevant data.

Fresh murine bone marrow cells were harvested from Balb/c female mouse femurs and cultured in media prepared for CFU-GM, including 1 percent of a spleen-conditioned medium. Hybrid cytokines, expressed as unpurified supernatants from transfected Vero E6 cells, were tested along with 100 ng/ml of rhG-CSF (from Collaborative Research) and the products of several transfections of unmodified human G-CSF cDNA.

Figure 5:
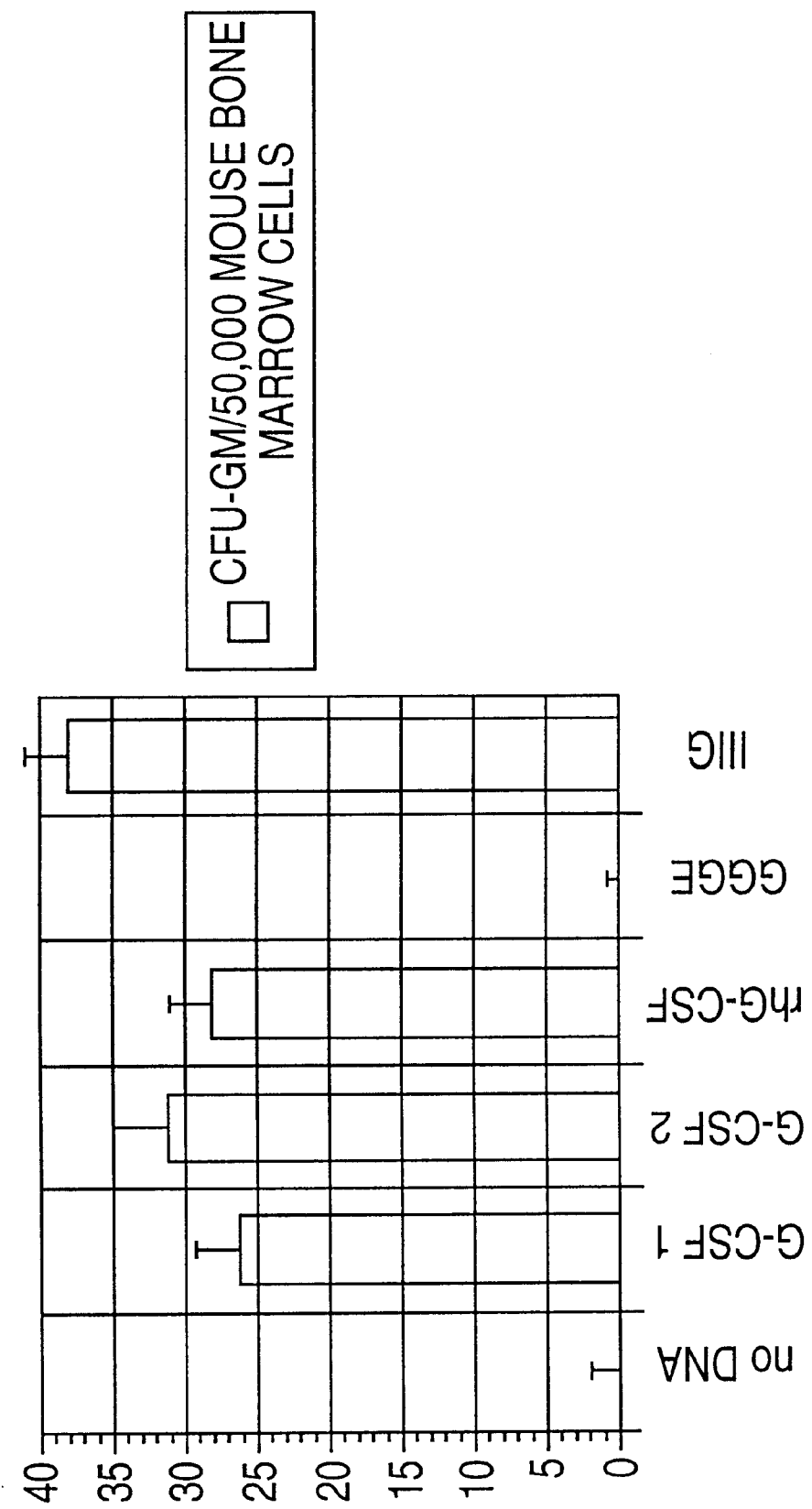
FIG. 5 shows the capacity of various cytokines to stimulate mouse bone marrow cells to form colonies of granulocyte/macrophage lineage.

Results shown in FIG. 5 indicate that although GGGE had minimal activity and supernatants from two G-CSF transfections stimulated an increase of approximately 25–30 colonies above control (no DNA), IIIG showed as much activity as either of the two G-CSF transfections.

```

-continued

```
     (ix) FEATURE:
          (A) NAME/KEY: G-CSF (B) LOCATION:

(C) IDENTIFICATION METHOD:

(D) OTHER INFORMATION:

(x) PUBLICATION INFORMATION:
          (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:1:

(xi) SEQUENCE DESCRIPTION:SEQ ID NO:1:

ACC CCC CTG GGC CCT GCC AGC TCC CTG CCC CAG AGC TTC CTG CTC AAG        48
Thr Pro Leu Gly Pro Ala Ser Ser Leu Pro Gln Ser Phe Leu Leu Lys
 5                  10                  15

CTG TGT GAG CAA GTG AGG AAG ATC CAG GGC GAT GGC GCA GCG CTC CAG        96
Cys Leu Glu Gln Val Arg Lys Ile Gln Gly Asp Gly Ala Ala Leu Gln
 20                  25                  30

GAG AAG TGC TTA GCC ACC TAC AAG CTG TGC CAC CCC GAG GAG CTG GTG       144
Glu Lys Cys Leu Ala Thr Tyr Lys Leu Cys His Pro Glu Glu Leu Val
 35                  40                  45

CTG CTC GGA CAC TCT CTG GGC ATC CCC TGG GCT CCC CTG AGC AGC TGC       192
Leu Leu Gly His Ser Leu Gly Ile Pro Trp Ala Pro Leu Ser Ser Cys
 50                  55                  60

CCC AGC CAG GCC CTG CAG CTG GCA GGC TGC TTG AGC CAA CTC CAT AGC       240
Pro Ser Gln Ala Leu Gln Leu Ala Gly Cys Leu Ser Gln Leu His Ser
 65                  70                  75                  80

GGC CTT TTC CTC TAC CAG GGG CTC CTG CAG GCC CTG GAA GGG ATC TCC       288
Gly Leu Phe Leu Tyr Gln Gly Leu Leu Gln Ala Leu Glu Gly Ile Ser
 85                  90                  95

CCC GAG TTG GGT CCC ACC TTG GAC ACA CTG CAG CTG GAC GTC GCC GAC       336
Pro Glu Leu Gly Pro Thr Leu Asp Thr Leu Gln Leu Asp Val Ala Asp
100                 105                 110

TTT GCC ACC ACC ATC TGG CAG CAG ATG GAA GAA CTG GGA ATG GCC CCT       384
Phe Ala Thr Thr Ile Trp Gln Gln Met Glu Glu Leu Gly Met Ala Pro
115                 120                 125

GCC CTG CAG CCC ACC CAG GGT GCC ATG CCG GCC TTC GCC TCT GCT TTC       432
Ala Leu Gln Pro Thr Gln Gly Ala Met Pro Ala Phe Ala Ser Ala Phe
130                 135                 140

CAG CGC CGG GCA GGA GGG GTC CTA GTT GCC TCC CAT CTG CAG AGC TTC       480
Gln Arg Arg Ala Gly Gly Val Leu Val Ala Ser His Leu Gln Ser Phe
145                 150                 155                 160

CTG GAG GTG TCG TAC CGC GTT CTA CGC CAC CTT GCC CAG CCC TGA            525
Leu Glu Val Ser Tyr Arg Val Leu Arg His Leu Ala Gln Pro ***
165                 170                 175
```

-continued (2) INFORMATION FOR SEQ ID NO:2:

(i) SEQUENCE CHARACTERISTICS:
        (A) LENGTH:540

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Fred Hutchinson Cancer Research Center (B) CLONE:

(viii) POSITION IN GENOME:
        (A) CHROMOSOME/SEGMENT:

(B) MAP POSITION:

(C) UNITS:

(ix) FEATURE:
        (A) NAME/KEY: LIF (B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:2:

(xi) SEQUENCE DESCRIPTION:SEQ ID NO:2:

```
CCT CTG CCC ATC ACC CCT GTC AAC GCC ACC TGT GCC ATA CGC CAC CCA      48
Pro Leu Pro Ile Thr Pro Val Asn Ala Thr Cys Ala Ile Arg His Pro
5                   10                  15

TGT CAC AAC AAC CTC ATG AAC CAG ATC AGG AGC CAA CTG GCA CAG CTC      96
Cys His Asn Asn Leu Met Asn Gln Ile Arg Ser Gln Leu Ala Gln Leu
20                  25                  30

AAT GGC AGT GCC AAT GCC CTC TTT ATT CTC TAT TAC ACA GCC CAG GGG     144
Asn Gly Ser Ala Asn Ala Leu Phe Ile Leu Tyr Tyr Thr Ala Gln Gly
35                  40                  45

GAG CCG TTC CCC AAC AAC CTG GAC AAG CTA TGT GGC CCC AAC GTG ACG     192
Glu Pro Phe Pro Asn Asn Leu Asp Lys Leu Cys Gly Pro Asn Val Thr
50                  55                  60

GAC TTC CCG CCC TTC CAC GCC AAC GGC ACG GAG AAG GCC AAG CTG GTG     240
Asp Phe Pro Pro Phe His Ala Asn Gly Thr Glu Lys Ala Lys Leu Val
65                  70                  75                  80

GAG CTG TAC CGC ATA GTC GTG TAC CTT GGC ACC TCC CTG GGC AAC ATC     288
Glu Leu Tyr Arg Ile Val Val Tyr Leu Gly Thr Ser Leu Gly Asn Ile
85                  90                  95

ACC CGG GAC CAG AAG ATC CTC AAC CCC AGT GCC CTC AGC CTC CAC AGC     336
Thr Arg Asp Gln Lys Ile Leu Asn Pro Ser Ala Leu Ser Leu His Ser
100                 105                 110

AAG CTC AAC GCC ACC GCC GAC ATC CTG CGA GGC CTC CTT AGC AAC GTG     384
Lys Leu Asn Ala Thr Ala Asp Ile Leu Arg Gly Leu Leu Ser Asn Val
115                 120                 125

CTG TGC CGC CTG TGC AGC AAG TAC CAC GTG GGC CAT GTG GAC GTG ACC     432
Leu Cys Arg Leu Cys Ser Lys Tyr His Val Gly His Val Asp Val Thr
130                 135                 140

TAC GGC CCT GAC ACC TCG GGT AAG GAT GTC TTC CAG AAG AAG AAG CTG     480
Tyr Gly Pro Asp Thr Ser Gly Lys Asp Val Phe Gln Lys Lys Lys Leu
145                 150                 155                 160

GGC TGT CAA CTC CTG GGG AAG TAT AAG CAG ATC ATC GCC GTG TTG GCC     528
Gly Cys Gln Leu Leu Gly Lys Tyr Lys Gln Ile Ile Ala Val Leu Ala
165                 170                 175

CAG GCC TTC TAG                                                     540
Gln Ala Phe ***
180
```

(2) INFORMATION FOR SEQ ID NO:3:

(i) SEQUENCE CHARACTERISTICS:
        (A) LENGTH:540

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

```
   (vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Fred Hutchinson Cancer Research Center (B) CLONE:

(viii) POSITION IN GENOME:
        (A) CHROMOSOME/SEGMENT:

(B) MAP POSITION:

(C) UNITS:

(ix) FEATURE:
        (A) NAME/KEY: IL-6

(B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:3:

(xi) SEQUENCE DESCRIPTION:SEQ ID NO:3:

GAA GAT TCC AAA GAT GTA GCC GCC CCA CAC AGA CAG CCA CTC ACC TCT        48
Glu Asp Ser Lys Asp Val Ala Ala Pro His Arg Gln Pro Leu Thr Ser
 5                  10                  15

TCA GAA CGA ATT GAC AAA CAA ATT CGG TAC ATC CTC GAC GGC ATC TCA        96
Ser Glu Arg Ile Asp Lys Gln Ile Arg Tyr Ile Leu Asp Gly Ile Ser
         20                  25                  30
```

```
GCC CTG AGA AAG GAG ACA TGT AAC AAG AGT AAC ATG TGT GAA AGC AGC        144
Ala Leu Arg Lys Glu Thr Cys Asn Lys Ser Asn Met Cys Glu Ser Ser
 35                  40                  45

AAA GAG GCA CTG GCA GAA AAC AAC CTG AAC CTT CCA AAG ATG GCT GAA        192
Lys Glu Ala Leu Ala Glu Asn Asn Leu Asn Leu Pro Lys Met Ala Glu
 50                  55                  60

AAA GAT GGA TGC TTC CAA TCT GGA TTC AAT GAG GAG ACT TGC CTG GTG        240
Lys Asp Gly Cys Phe Gln Ser Gly Phe Asn Glu Glu Thr Cys Leu Val
 65                  70                  75                  80

AAA ATC ATC ACT GGT CTT TTG GAG TTT GAG GTA TAC CTA GAG TAC CTC        288
Lys Ile Ile Thr Gly Leu Leu Glu Phe Glu Val Tyr Leu Glu Tyr Leu
 85                  90                  95

CAG AAC AGA TTT GAG AGT AGT GAG GAA CAA GCC AGA GCT GTC CAG ATG        336
Gln Asn Arg Phe Glu Ser Ser Glu Glu Gln Ala Arg Ala Val Gln Met
100                 105                 110

AGT ACA AAA GTC CTG ATC CAG TTC CTG CAG AAA AAG GCA AAG AAT CTA        384
Ser Thr Lys Val Leu Ile Gln Phe Leu Gln Lys Lys Ala Lys Asn Leu
115                 120                 125

GAT GCA ATA ACC ACC CCT GAC CCA ACC ACA AAT GCC AGC CTG CTG ACG        432
Asp Ala Ile Thr Thr Pro Asp Pro Thr Thr Asn Ala Ser Leu Leu Thr
130                 135                 140

AAG CTG CAG GCA CAG AAC CAG TGG CTG CAG GAC ATG ACA ACT CAT CTC        480
Lys Leu Gln Ala Gln Asn Gln Trp Leu Gln Asp Met Thr Thr His Leu
145                 150                 155                 160

ATT CTG CGC AGC TTT AAG GAG TTC CTG CAG TCC AGC CTG AGG GCT CTT        528
Ile Leu Arg Ser Phe Lys Glu Phe Leu Gln Ser Ser Leu Arg Ala Leu
165                 170                 175

CGG CAA ATG TAG                                                        540
Arg Gln Met ***
180
```

(2) INFORMATION FOR SEQ ID NO:4:

(i) SEQUENCE CHARACTERISTICS:
        (A) LENGTH:591

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

```
    (vii) IMMEDIATE SOURCE:
          (A) LIBRARY:Fred Hutchinson Cancer Research Center (B) CLONE:

(viii) POSITION IN GENOME:
          (A) CHROMOSOME/SEGMENT:

(B) MAP POSITION:

(C) UNITS:

(ix) FEATURE:
          (A) NAME/KEY: OSM (B) LOCATION:

(C) IDENTIFICATION METHOD:

(D) OTHER INFORMATION:

(x) PUBLICATION INFORMATION:
          (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:4:

(xi) SEQUENCE DESCRIPTION:SEQ ID NO:4:

GCG GCT ATA GGC AGC TGC TCG AAA GAG TAC CGC GTG CTC CTT GGC CAG        48
Ala Ala Ile Gly Ser Cys Ser Lys Glu Tyr Arg Val Leu Leu Gly Gln
5                   10                  15

CTC CAG AAG CAG ACA GAT CTC ATG CAG GAC ACC AGC AGA CTC CTG GAC        96
Leu Gln Lys Gln Thr Asp Leu Met Gln Asp Thr Ser Arg Leu Leu Asp
20                  25                  30

CCC TAT ATA CGT ATC CAA GGC CTG GAT GTT CCT AAA CTG AGA GAG CAC       144
Pro Tyr Ile Arg Ile Gln Gly Leu Asp Val Pro Lys Leu Arg Glu His
35                  40                  45

TGC AGG GAG CGC CCC GGG GCC TTC CCC AGT GAG GAG ACC CTG AGG GGG       192
Cys Arg Glu Arg Pro Gly Ala Phe Pro Ser Glu Glu Thr Leu Arg Gly
50                  55                  60

CTG GGC AGG CGG GGC TTC CTG CAG ACC CTC AAT GCC ACA CTG GGC TGC       240
Leu Gly Arg Arg Gly Phe Leu Gln Thr Leu Asn Ala Thr Leu Gly Cys
65                  70                  75                  80

GTC CTG CAC AGA CTG GCC GAC TTA GAG CAG CGC CTC CCC AAG GCC CAG       288
Val Leu His Arg Leu Ala Asp Leu Glu Gln Arg Leu Pro Lys Ala Gln
85                  90                  95

GAT TTG GAG AGG TCT GGG CTG AAC ATC GAG GAC TTG GAG AAG CTG CAG       336
Asp Leu Glu Arg Ser Gly Leu Asn Ile Glu Asp Leu Glu Lys Leu Gln
100                 105                 110
```

```
ATG GCG AGG CCG AAC ATC CTC GGG CTC AGG AAC AAC ATC TAC TGC ATG      384
Met Ala Arg Pro Asn Ile Leu Gly Leu Arg Asn Asn Ile Tyr Cys Met
115                 120                 125

GCC CAG CTG CTG GAC AAC TCA GAC ACG GCT GAG CCC ACG AAG GCT GGC      432
Ala Gln Leu Leu Asp Asn Ser Asp Thr Ala Glu Pro Thr Lys Ala Gly
130                 135                 140

CGG GGG GCC TCT CAG CCG CCC ACC CCC ACC CCT GCC TCG GAT GCT TTT      480
Arg Gly Ala Ser Gln Pro Pro Thr Pro Thr Pro Ala Ser Asp Ala Phe
145                 150                 155                 160

CAG CGC AAG CTG GAG GGC TGC AGG TTC CTG CAT GGC TAC CAT CGC TTC      528
Gln Arg Lys Leu Glu Gly Cys Arg Phe Leu His Gly Tyr His Arg Phe
165                 170                 175

ATG CAC TCA GTG GGG CGG GTC TTC AGC AAG TGG GGG GAG AGC CCG AAC      576
Met His Ser Val Gly Arg Val Phe Ser Lys Trp Gly Glu Ser Pro Asn
180                 185                 190

CGG AGC CGG AGA TAA                                                  591
Arg Ser Arg Arg ***
195
```

(2) INFORMATION FOR SEQ ID NO:5:

(i) SEQUENCE CHARACTERISTICS:
        (A) LENGTH:603

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Fred Hutchinson Cancer Research Center (B) CLONE:

(viii) POSITION IN GENOME:
        (A) CHROMOSOME/SEGMENT:

(B) MAP POSITION:

(C) UNITS:

(ix) FEATURE:
    (A) NAME/KEY: CNTF
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:5:

(xi) SEQUENCE DESCRIPTION:SEQ ID NO:5:

```
ATG GCT TTC ACA GAG CAT TCA CCG CTG ACC CCT CAC CGT CGG GAC CTC        48
Met Ala Phe Thr Glu His Ser Pro Leu Thr Pro His Arg Arg Asp Leu
5                  10                  15

TGT AGC CGC TCT ATC TGG CTA GCA AGG AAG ATT CGT TCA GAC CTG ACT        96
Cys Ser Arg Ser Ile Trp Leu Ala Arg Lys Ile Arg Ser Asp Leu Thr
20                  25                  30

GCT CTT ACG GAA TCC TAT GTG AAG CAT CAG GGC CTG AAC AAG AAC ATC       144
Ala Leu Thr Glu Ser Tyr Val Lys His Gln Gly Leu Asn Lys Asn Ile
35                  40                  45

AAC CTG GAC TCT GCG GAT GGG ATG CCA GTG GCA AGC ACT GAT CAG TGG       192
Asn Leu Asp Ser Ala Asp Gly Met Pro Val Ala Ser Thr Asp Gln Trp
50                  55                  60

AGT GAG CTG ACC GAG GCA GAG CGA CTC CAA GAG AAC CTT CAA GCT TAT       240
Ser Glu Leu Thr Glu Ala Glu Arg Leu Gln Glu Asn Leu Gln Ala Tyr
65                  70                  75                  80

CGT ACC TTC CAT GTT TTG TTG GCC AGG CTC TTA GAA GAC CAG CAG GTG       288
Arg Thr Phe His Val Leu Leu Ala Arg Leu Leu Glu Asp Gln Gln Val
85                  90                  95

CAT TTT ACC CCA ACC GAA GGT GAC TTC CAT CAA GCT ATA CAT ACC CTT       336
His Phe Thr Pro Thr Glu Gly Asp Phe His Gln Ala Ile His Thr Leu
100                 105                 110

CTT CTC CAA GTC GCT GCC TTT GCA TAC CAG ATA GAG GAG TTA ATG ATA       384
Leu Leu Gln Val Ala Ala Phe Ala Tyr Gln Ile Glu Glu Leu Met Ile
115                 120                 125

CTC CTG GAA TAC AAG ATC CCC CGC AAT GAG GCT GAT GGG ATG CCT ATT       432
Leu Leu Glu Tyr Lys Ile Pro Arg Asn Glu Ala Asp Gly Met Pro Ile
130                 135                 140

AAT GTT GGA GAT GGT GGT CTC TTT GAG AAG AAG CTG TGG GGC CTA AAG       480
Asn Val Gly Asp Gly Gly Leu Phe Glu Lys Lys Leu Trp Gly Leu Lys
145                 150                 155                 160

GTG CTG CAG GAG CTT TCA CAG TGG ACA GTA AGG TCC ATC CAT GAC CTT       528
Val Leu Gln Glu Leu Ser Gln Trp Thr Val Arg Ser Ile His Asp Leu
165                 170                 175
```

```
CGT TTC ATT TCT TCT CAT CAG ACT GGG ATC CCA GCA CGT GGG AGC CAT          576
Arg Phe Ile Ser Ser His Gln Thr Gly Ile Pro Ala Arg Gly Ser His
180             185                 190

TAT ATT GCT AAC AAC AAG AAA ATG TAG                                     603
Tyr Ile Ala Asn Asn Lys Lys Met ***
 95              200
```

(2) INFORMATION FOR SEQ ID NO:6:

(i) SEQUENCE CHARACTERISTICS:
        (A) LENGTH:537

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Fred Hutchinson Cancer Research Center (B) CLONE:

(viii) POSITION IN GENOME:
        (A) CHROMOSOME/SEGMENT:

(B) MAP POSITION:

(C) UNITS:

(ix) FEATURE:
        (A) NAME/KEY: IL-11

(B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:6:

(xi) SEQUENCE DESCRIPTION:SEQ ID NO:6:

```
CCT GGG CCA CCA CCT GGC CCC CCT CGA GTT TCC CCA GAC CCT CGG GCC     48
Pro Gly Pro Pro Pro Gly Pro Pro Arg Val Ser Pro Asp Pro Arg Ala
5                   10                  15

GAG CTG GAC AGC ACC GTG CTC CTG ACC CGC TCT CTC CTG GCG GAC ACG     96
Glu Leu Asp Ser Thr Val Leu Leu Thr Arg Ser Leu Leu Ala Asp Thr
20                  25                  30

CGG CAG CTG GCT GCA CAG CTG AGG GAC AAA TTC CCA GCT GAC GGG GAC    144
Arg Gln Leu Ala Ala Gln Leu Arg Asp Lys Phe Pro Ala Asp Gly Asp
35                  40                  45

CAC AAC CTG GAT TCC CTG CCC ACC CTG GCC ATG AGT GCG GGG GCA CTG    192
His Asn Leu Asp Ser Leu Pro Thr Leu Ala Met Ser Ala Gly Ala Leu
50                  55                  60

GGA GCT CTA CAG CTC CCA GGT GTG CTG ACA AGG CTG CGA GCG GAC CTA    240
Gly Ala Leu Gln Leu Pro Gly Val Leu Thr Arg Leu Arg Ala Asp Leu
65                  70                  75                  80

CTG TCC TAC CTG CGG CAC GTG CAG TGG CTG CGC CGG GCA GGT GGC TCT    288
Leu Ser Tyr Leu Arg His Val Gln Trp Leu Arg Arg Ala Gly Gly Ser
85                  90                  95

TCC CTG AAG ACC CTG GAG CCC GAG CTG GGC ACC CTG CAG GCC CGA CTG    336
Ser Leu Lys Thr Leu Glu Pro Glu Leu Gly Thr Leu Gln Ala Arg Leu
100                 105                 110

GAC CGG CTG CTG CGC CGG CTG CAG CTC CTG ATG TCC CGC CTG GCC CTG    384
Asp Arg Leu Leu Arg Arg Leu Gln Leu Leu Met Ser Arg Leu Ala Leu
115                 120                 125

CCC CAG CCA CCC CCG GAC CCG CCG GCG CCC CCG CTG GCG CCC CCC TCC    432
Pro Gln Pro Pro Pro Asp Pro Pro Ala Pro Pro Leu Ala Pro Pro Ser
130                 135                 140

TCA GCC TGG GGG GGC ATC AGG GCC GCC CAC GCC ATC CTG GGG GGG CTG    480
Ser Ala Trp Gly Gly Ile Arg Ala Ala His Ala Ile Leu Gly Gly Leu
145                 150                 155                 160

CAC CTG ACA CTT GAC TGG GCC GTG AGG GGA CTG CTG CTG CTG AAG ACT    528
His Leu Thr Leu Asp Trp Ala Val Arg Gly Leu Leu Leu Leu Lys Thr
165                 170                 175

CGG CTG TGA                                                        537
Arg Leu ***
179
```

(2) INFORMATION FOR SEQ ID NO:7:

(i) SEQUENCE CHARACTERISTICS:
  (A) LENGTH:558

(B) TYPE:nucleic acid (C) STRANDEDNESS:double stranded (D) TOPOLOGY:linear

```
    (ii) MOLECULE TYPE:cDNA to mRNA (iii) HYPOTHETICAL:no (iv) ANTI-SENSE:no (v) FRAGMENT TYPE:

(vi) ORIGINAL SOURCE:
         (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
         (A) LIBRARY:

(B) CLONE:

(viii) POSITION IN GENOME:
         (A) CHROMOSOME/SEGMENT:

(B) MAP POSITION:

(C) UNITS:

(ix) FEATURE:
         (A) NAME/KEY:

(B) LOCATION:

(C) IDENTIFICATION METHOD:

(D) OTHER INFORMATION:

(x) PUBLICATION INFORMATION:
         (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:7:
```

(xi) SEQUENCE DESCRIPTION:SEQ ID NO:7:

```
AAG CTT GTA CCT CCA GGA GAA GAT TCC AAA GAT GTA GCC GCC CCA CAC      48
Lys Leu Val Pro Pro Gly Glu Asp Ser Lys Asp Val Ala Ala Pro His
 5               10                  15

AGA CAG CCA CTC ACC TCT TCA GAA CGA ATT GAC AAA CAA ATT CGG TAC      96
Arg Gln Pro Leu Thr Ser Ser Glu Arg Ile Asp Lys Gln Ile Arg Tyr
20                  25                  30

ATC CTC GAC GGC ATC TCA GCC CTG AGA AAG GAG ACA TGT AAC AAG AGT     144
Ile Leu Asp Gly Ile Ser Ala Leu Arg Lys Glu Thr Cys Asn Lys Ser
35                  40                  45

AAC ATG TGT GAA AGC AGC AAA GAG GCA CTG GCA GAA AAC AAC CTG AAC     192
Asn Met Cys Glu Ser Ser Lys Glu Ala Leu Ala Glu Asn Asn Leu Asn
50                  55                  60

CTT CCA AAG ATG GCT GAA AAA GAT GGA TGC TTC CAA TCT GGA TTC AAT     240
Leu Pro Lys Met Ala Glu Lys Asp Gly Cys Phe Gln Ser Gly Phe Asn
65                  70                  75                  80

GAG GAG ACT TGC CTG GTG AAA ATC ATC ACT GGT CTT TTG GAG TTT GAG     288
Glu Glu Thr Cys Leu Val Lys Ile Ile Thr Gly Leu Leu Glu Phe Glu
85                  90                  95

GTA TAC CTA GAG TAC CTC CAG AAC AGA TTT GAG AGT AGT GAG GAA CAA     336
Val Tyr Leu Glu Tyr Leu Gln Asn Arg Phe Glu Ser Ser Glu Glu Gln
100                 105                 110

GCC AGA GCT GTG CAG ATG AGT ACA AAA GTC CTG ATC CAG TTC CTG CAG     384
Ala Arg Ala Val Gln Met Ser Thr Lys Val Leu Ile Gln Phe Leu Gln
115                 120                 125

AAA AAG GCA AAG AAT CTA GAT GCA ATA ACC ACC CCT GAC CCC ACC CAG     432
Lys Lys Ala Lys Asn Leu Asp Ala Ile Thr Thr Pro Asp Pro Thr Gln
130                 135                 140

GGT GCC ATG CCG GCC TTC GCT AGC GCT TTC CAG CGC CGG GCA GGA GGG     480
Gly Ala Met Pro Ala Phe Ala Ser Ala Phe Gln Arg Arg Ala Gly Gly
145                 150                 155                 160

GTC CTA GTT GCC TCC CAT CTG CAG AGC TTC CTG GAG GTG TCG TAC CGC     528
Val Leu Val Ala Ser His Leu Gln Ser Phe Leu Glu Val Ser Tyr Arg
165                 170                 175

GTT CTA CGC CAC CTT GCC CAG CCC TAG GAT                             558
Val Leu Arg His Leu Ala Gln Pro *** Asp
180                 185
```

(2) INFORMATION FOR SEQ ID NO:8:

(i) SEQUENCE CHARACTERISTICS:
        (A) LENGTH:588

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Cell Therapeutics, Inc.

(B) CLONE:

(viii) POSITION IN GENOME:
        (A) CHROMOSOME/SEGMENT:

(B) MAP POSITION:

(C) UNITS:

(ix) FEATURE:
        (A) NAME/KEY:

(B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:8:

(xi) SEQUENCE DESCRIPTION:SEQ ID NO:8:

```
AAG CTT CCT CTG CCC ATC ACC CCT GTC AAC GCC ACC TGT GCC ATA CGC         48
Lys Leu Pro Leu Pro Ile Thr Pro Val Asn Ala Thr Cys Ala Ile Arg
 5                  10                  15

CAC CCA TGT CAC AAC AAC CTC ATG AAC CAG ATC AGG AGC CAA CTG GCA         96
His Pro Cys His Asn Asn Leu Met Asn Gln Ile Arg Ser Gln Leu Ala
 20                  25                  30

CAG CTC AAT GGC AGT GCC AAT GCC CTC TTT ATT CTC TAT TAC ACA GCC        144
Gln Leu Asn Gly Ser Ala Asn Ala Leu Phe Ile Leu Tyr Tyr Thr Ala
 35                  40                  45

CAG GGG GAG CCG TTC CCC AAC AAC CTG GAC AAG CTA TGT GGC CCC AAC        192
Gln Gly Glu Pro Phe Pro Asn Asn Leu Asp Lys Leu Cys Gly Pro Asn
 50                  55                  60
```

```
GTG ACG GAC TTC CCG CCC TTC CAC GCC AAC GGC ACG GAG AAG GCC AAG        240
Val Thr Asp Phe Pro Pro Phe His Ala Asn Gly Thr Glu Lys Ala Lys
 65              70                  75                  80

CTG GTG GAG CTG TAC CGC ATA GTC GTG TAC CTT GGC ACC TCC CTG GGC        288
Leu Val Glu Leu Tyr Arg Ile Val Val Tyr Leu Gly Thr Ser Leu Gly
 85              90                  95

AAC ATC ACC CGG GAC CAG AAG ATC CTC AAC CCC AGT GCC CTC AGC CTC        336
Asn Ile Thr Arg Asp Gln Lys Ile Leu Asn Pro Ser Ala Leu Ser Leu
100             105                 110

CAC AGC AAG CTC AAC GCC ACC GCC GAC ATC CTG CGA GGC CTC CTT AGC        384
His Ser Lys Leu Asn Ala Thr Ala Asp Ile Leu Arg Gly Leu Leu Ser
115             120                 125

AAC GTG CTG TGC CGC CTG TGC AGC AAG TAC CAC GTG GGC CAT GTG GAC        432
Asn Val Leu Cys Arg Leu Cys Ser Lys Tyr His Val Gly His Val Asp
130             135                 140

GTG ACC TAC GGT CCG GAC CCA ACC ACA AAT GCC AGC CTG CTG ACG AAG        480
Val Thr Tyr Gly Pro Asp Pro Thr Thr Asn Ala Ser Leu Leu Thr Lys
145             150                 155                 160

CTG CAG GCA CAG AAC CAG TGG CTG CAG GAC ATG ACA ACT CAT CTC ATT        528
Leu Gln Ala Gln Asn Gln Trp Leu Gln Asp Met Thr Thr His Leu Ile
165             170                 175

CTG CGC AGC TTT AAG GAG TTC CTG CAG TCC AGC CTG AGG GCT CTT CGG        576
Leu Arg Ser Phe Lys Glu Phe Leu Gln Ser Ser Leu Arg Ala Leu Arg
180             185                 190

CAA ATG TAG GAT                                                        588
Gln Met *** Asp
195
```

(2) INFORMATION FOR SEQ ID NO:9:

(i) SEQUENCE CHARACTERISTICS:
        (A) LENGTH:582

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

```
    (vii) IMMEDIATE SOURCE:
          (A) LIBRARY:Cell Therapeutics, Inc.

(B) CLONE:

(viii) POSITION IN GENOME:
          (A) CHROMOSOME/SEGMENT:

(B) MAP POSITION:

(C) UNITS:

(ix) FEATURE:
          (A) NAME/KEY:

(B) LOCATION:

(C) IDENTIFICATION METHOD:

(D) OTHER INFORMATION:

(x) PUBLICATION INFORMATION:
          (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:9:

(xi) SEQUENCE DESCRIPTION:SEQ ID NO:9:

AAG CTT CCT CTG CCC ATC ACC CCT GTC AAC GCC ACC TGT GCC ATA CGC      48
Lys Leu Pro Leu Pro Ile Thr Pro Val Asn Ala Thr Cys Ala Ile Arg
 5                  10                  15

CAC CCA TGT CAC AAC AAC CTC ATG AAC CAG ATC AGG AGC CAA CTG GCA      96
His Pro Cys His Asn Asn Leu Met Asn Gln Ile Arg Ser Gln Leu Ala
20                  25                  30

CAG CTC AAT GGC AGT GCC AAT GCC CTC TTT ATT CTC TAT TAC ACA GCC     144
Gln Leu Asn Gly Ser Ala Asn Ala Leu Phe Ile Leu Tyr Tyr Thr Ala
35                  40                  45

CAG GGG GAG CCG TTC CCC AAC AAC CTG GAC AAG CTA TGT GGC CCC AAC     192
Gln Gly Glu Pro Phe Pro Asn Asn Leu Asp Lys Leu Cys Gly Pro Asn
50                  55                  60

GTG ACG GAC TTC CCG CCC TTC CAC GCC AAC GGC ACG GAG AAG GCC AAG     240
Val Thr Asp Phe Pro Pro Phe His Ala Asn Gly Thr Glu Lys Ala Lys
65                  70                  75                  80

CTG GTG GAG CTG TAC CGC ATA GTC GTG TAC CTT GGC ACC TCC CTG GGC     288
Leu Val Glu Leu Tyr Arg Ile Val Val Tyr Leu Gly Thr Ser Leu Gly
85                  90                  95

AAC ATC ACC CGG GAC CAG AAG ATC CTC AAC CCC AGT GCC CTC AGC CTC     336
Asn Ile Thr Arg Asp Gln Lys Ile Leu Asn Pro Ser Ala Leu Ser Leu
100                 105                 110
```

```
CAC AGC AAG CTC AAC GCC ACC GCC GAC ATC CTG CGA GGC CTC CTT AGC        384
His Ser Lys Leu Asn Ala Thr Ala Asp Ile Leu Arg Gly Leu Leu Ser
115                 120                 125

AAC GTG CTG TGC CGC CTG TGC AGC AAG TAC CAC GTG GGC CAT GTG GAC        432
Asn Val Leu Cys Arg Leu Cys Ser Lys Tyr His Val Gly His Val Asp
130                 135                 140

GTG ACC TAC GGT CCG GAC ACA AAT GCC AGC CTG CTG ACG AAG CTG CAG        480
Val Thr Tyr Gly Pro Asp Thr Asn Ala Ser Leu Leu Thr Lys Leu Gln
145                 150                 155                 160

GCA CAG AAC CAG TGG CTG CAG GAC ATG ACA ACT CAT CTC ATT CTG CGC        528
Ala Gln Asn Gln Trp Leu Gln Asp Met Thr Thr His Leu Ile Leu Arg
165                 170                 175

AGC TTT AAG GAG TTC CTG CAG TCC AGC CTG AGG GCT CTT CGG CAA ATG        576
Ser Phe Lys Glu Phe Leu Gln Ser Ser Leu Arg Ala Leu Arg Gln Met
180                 185                 190

TAG GAT                                                                582
*** Asp
194
```

(2) INFORMATION FOR SEQ ID NO:10:

(i) SEQUENCE CHARACTERISTICS:
        (A) LENGTH:528

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Cell Therapeutics, Inc.

(B) CLONE:

(viii) POSITION IN GENOME:
        (A) CHROMOSOME/SEGMENT:

(B) MAP POSITION:

(C) UNITS:

(ix) FEATURE:
    (A) NAME/KEY:

(B) LOCATION:

(C) IDENTIFICATION METHOD:

(D) OTHER INFORMATION:

(x) PUBLICATION INFORMATION:
    (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:10:

(xi) SEQUENCE DESCRIPTION:SEQ ID NO:10:

```
AAG CTT GTA CCT CCA GGA GAA GAT TCC AAA GAT GTA GCC GCC CCA CAC        48
Lys Leu Val Pro Pro Gly Glu Asp Ser Lys Asp Val Ala Ala Pro His
5                   10                  15

AGA CAG CCA CTC ACC TCT TCA GAA CGA ATT GAC AAA CAA ATT CGG TAC        96
Arg Gln Pro Leu Thr Ser Ser Glu Arg Ile Asp Lys Gln Ile Arg Tyr
20                  25                  30

ATC CTC GAC GGC ATC TCA GCC CTG AGA AAG GAG ACA TGT AAC AAG AGT       144
Ile Leu Asp Gly Ile Ser Ala Leu Arg Lys Glu Thr Cys Asn Lys Ser
35                  40                  45

AAC ATG TGT GAA AGC AGC AAA GAG GCA CTG GCA GAA AAC AAC CTG AAC       192
Asn Met Cys Glu Ser Ser Lys Glu Ala Leu Ala Glu Asn Asn Leu Asn
50                  55                  60

CTT CCA AAG ATG GCT GAA AAA GAT GGA TGC TTC CAA TCT GGA TTC AAT       240
Leu Pro Lys Met Ala Glu Lys Asp Gly Cys Phe Gln Ser Gly Phe Asn
65                  70                  75                  80

GAG GAG ACT TGC CTG GTG AAA ATC ATC ACT GGT CTT TTG GAG TTT GAG       288
Glu Glu Thr Cys Leu Val Lys Ile Ile Thr Gly Leu Leu Glu Phe Glu
85                  90                  95

GTA TAC CTA GAG TAC CTC CAG AAC AGA TTT GAG AGT AGT GAG GAA CAA       336
Val Tyr Leu Glu Tyr Leu Gln Asn Arg Phe Glu Ser Ser Glu Glu Gln
100                 105                 110

GCC AGA GCT GTG CAG ATG AGT ACA AAA GTC CTG ATC CAG TTC CTG CAG       384
Ala Arg Ala Val Gln Met Ser Thr Lys Val Leu Ile Gln Phe Leu Gln
115                 120                 125

AAA AAG GCA AAG AAT CTA GAT GCA ATA ACC ACC CCT GAT CCG ACC           432
Lys Lys Ala Lys Asn Leu Asp Ala Ile Thr Thr Pro Asp Pro Asp Thr
130                 135                 140

TCG GGT AAG GAT GTC TTC CAG AAG AAG AAG CTG GGC TGT CAA CTC CTG       480
Ser Gly Lys Asp Val Phe Gln Lys Lys Lys Leu Gly Cys Gln Leu Leu
145                 150                 155                 160

GGG AAG TAT AAG CAG ATC ATC GCC GTG TTG GCC CAG GCC TTC TAG GAT       528
Gly Lys Tyr Lys Gln Ile Ile Ala Val Leu Ala Gln Ala Phe *** Asp
165                 170                 175
```

```
(2) INFORMATION FOR SEQ ID NO:11:

(i) SEQUENCE CHARACTERISTICS:
        (A) LENGTH:522

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Cell Therapeutics, Inc.

(B) CLONE:

(viii) POSITION IN GENOME:
        (A) CHROMOSOME/SEGMENT:

(B) MAP POSITION:

(C) UNITS:

(ix) FEATURE:
        (A) NAME/KEY:

(B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:
```

(H) DOCUMENT NUMBER:

(I) FILING DATE:

(J) PUBLICATION DATE:

(K) RELEVANT RESIDUES IN SEQ ID NO:11:

(xi) SEQUENCE DESCRIPTION:SEQ ID NO:11:

```
AAG CTT GTA CCT CCA GGA GAA GAT TCC AAA GAT GTA GCC GCC CCA CAC        48
Lys Leu Val Pro Pro Gly Glu Asp Ser Lys Asp Val Ala Ala Pro His
 5                  10                  15

AGA CAG CCA CTC ACC TCT TCA GAA CGA ATT GAC AAA CAA ATT CGG TAC        96
Arg Gln Pro Leu Thr Ser Ser Glu Arg Ile Asp Lys Gln Ile Arg Tyr
 20                  25                  30

ATC CTC GAC GGC ATC TCA GCC CTG AGA AAG GAG ACA TGT AAC AAG AGT       144
Ile Leu Asp Gly Ile Ser Ala Leu Arg Lys Glu Thr Cys Asn Lys Ser
 35                  40                  45

AAC ATG TGT GAA AGC AGC AAA GAG GCA CTG GCA GAA AAC AAC CTG AAC       192
Asn Met Cys Glu Ser Ser Lys Glu Ala Leu Ala Glu Asn Asn Leu Asn
 50                  55                  60

CTT CCA AAG ATG GCT GAA AAA GAT GGA TGC TTC CAA TCT GGA TTC AAT       240
Leu Pro Lys Met Ala Glu Lys Asp Gly Cys Phe Gln Ser Gly Phe Asn
 65                  70                  75                  80

GAG GAG ACT TGC CTG GTG AAA ATC ATC ACT GGT CTT TTG GAG TTT GAG       288
Glu Glu Thr Cys Leu Val Lys Ile Ile Thr Gly Leu Leu Glu Phe Glu
 85                  90                  95

GTA TAC CTA GAG TAC CTC CAG AAC AGA TTT GAG AGT AGT GAG GAA CAA       336
Val Tyr Leu Glu Tyr Leu Gln Asn Arg Phe Glu Ser Ser Glu Glu Gln
100                 105                 110

GCC AGA GCT GTG CAG ATG AGT ACA AAA GTC CTG ATC CAG TTC CTG CAG       384
Ala Arg Ala Val Gln Met Ser Thr Lys Val Leu Ile Gln Phe Leu Gln
115                 120                 125

AAA AAG GCA AAG AAT CTA GAT GCA ATA ACC ACT CCG GAC ACC TCG GGT       432
Lys Lys Ala Lys Asn Leu Asp Ala Ile Thr Thr Pro Asp Thr Ser Gly
130                 135                 140

AAG GAT GTC TTC CAG AAG AAG AAG CTG GGC TGT CAA CTC CTG GGG AAG       480
Lys Asp Val Phe Gln Lys Lys Lys Leu Gly Cys Gln Leu Leu Gly Lys
145                 150                 155                 160

TAT AAG CAG ATC ATC GCC GTG TTG GCC CAG GCC TTC TAG GAT                522
Tyr Lys Gln Ile Ile Ala Val Leu Ala Gln Ala Phe ***  Asp
165                 170
```

(2) INFORMATION FOR SEQ ID NO:12:

(i) SEQUENCE CHARACTERISTICS:
        (A) LENGTH:558

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

```
       (vi) ORIGINAL SOURCE:
             (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
             (A) LIBRARY:Cell Therapeutics, Inc.

(B) CLONE:

(viii) POSITION IN GENOME:
             (A) CHROMOSOME/SEGMENT:

(B) MAP POSITION:

(C) UNITS:

(ix) FEATURE:
             (A) NAME/KEY:

(B) LOCATION:

(C) IDENTIFICATION METHOD:

(D) OTHER INFORMATION:

(x) PUBLICATION INFORMATION:
             (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:12:

(xi) SEQUENCE DESCRIPTION:SEQ ID NO:12:

AAG CTT GTA CCT CCA GGA GAA GAT TCC AAA GAT GTA GCC GCC CCA CAC        48
Lys Leu Val Pro Pro Gly Glu Asp Ser Lys Asp Val Ala Ala Pro His
 5                  10                  15

AGA CAG CCA CTC ACC TCT TCA GAA CGA ATT GAC AAA CAA ATT CGG TAC        96
Arg Gln Pro Leu Thr Ser Ser Glu Arg Ile Asp Lys Gln Ile Arg Tyr
20                  25                  30
```

```
ATC CTC GAC GGC ATC TCA GCC CTG AGA AAG GAG ACA TGT AAC AAG AGT        144
Ile Leu Asp Gly Ile Ser Ala Leu Arg Lys Glu Thr Cys Asn Lys Ser
35                  40                  45

AAC ATG TGT GAA AGC AGC AAA GAG GCA CTG GCA GAA AAC AAC CTG AAC        192
Asn Met Cys Glu Ser Ser Lys Glu Ala Leu Ala Glu Asn Asn Leu Asn
50                  55                  60

CTT CCA AAG ATG GCT GAA AAA GAT GGA TGC TTC CAA TCT GGA TTC AAT        240
Leu Pro Lys Met Ala Glu Lys Asp Gly Cys Phe Gln Ser Gly Phe Asn
65                  70                  75                  80

GAG GAG ACT TGC CTG GTG AAA ATC ATC ACT GGT CTT TTG GAG TTT GAG        288
Glu Glu Thr Cys Leu Val Lys Ile Ile Thr Gly Leu Leu Glu Phe Glu
85                  90                  95

GTA TAC CTA GAG TAC CTC CAG AAC AGA TTT GAG AGT AGT GAG GAA CAA        336
Val Tyr Leu Glu Tyr Leu Gln Asn Arg Phe Glu Ser Ser Glu Glu Gln
100                 105                 110

GCC AGA GCT GTG CAG ATG AGT ACA AAA GTC CTG ATC CAG TTC CTG CAG        384
Ala Arg Ala Val Gln Met Ser Thr Lys Val Leu Ile Gln Phe Leu Gln
115                 120                 125

AAA AAG GCA AAG AAT CTA GAT GCA ATA ACC ACC CCT GAT CCG GAC CAG        432
Lys Lys Ala Lys Asn Leu Asp Ala Ile Thr Thr Pro Asp Pro Asp Gln
130                 135                 140

GGT GCC ATG CCG GCC TTC GCC TCT GCT TTC CAG CGC CGG GCA GGA GGG        480
Gly Ala Met Pro Ala Phe Ala Ser Ala Phe Gln Arg Arg Ala Gly Gly
145                 150                 155                 160

GTC CTA GTT GCC TCC CAT CTG CAG AGC TTC CTG GAG GTG TCG TAC CGC        528
Val Leu Val Ala Ser His Leu Gln Ser Phe Leu Glu Val Ser Tyr Arg
165                 170                 175

GTT CTA CGC CAC CTT GCC CAG CCC TAG GAT                                558
Val Leu Arg His Leu Ala Gln Pro *** Asp
180                 185
```

(2) INFORMATION FOR SEQ ID NO:13:

(i) SEQUENCE CHARACTERISTICS:
        (A) LENGTH:555

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

```
    (vii) IMMEDIATE SOURCE:
          (A) LIBRARY:Cell Therapeutics, Inc.

(B) CLONE:

(viii) POSITION IN GENOME:
          (A) CHROMOSOME/SEGMENT:

(B) MAP POSITION:

(C) UNITS:

(ix) FEATURE:
          (A) NAME/KEY:

(B) LOCATION:

(C) IDENTIFICATION METHOD:

(D) OTHER INFORMATION:

(x) PUBLICATION INFORMATION:
          (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:13:

(xi) SEQUENCE DESCRIPTION:SEQ ID NO:13:

AAG CTT GTA CCT CCA GGA GAA GAT TCC AAA GAT GTA GCC GCC CCA CAC        48
Lys Leu Val Pro Pro Gly Glu Asp Ser Lys Asp Val Ala Ala Pro His
 5                  10                  15

AGA CAG CCA CTC ACC TCT TCA GAA CGA ATT GAC AAA CAA ATT CGG TAC        96
Arg Gln Pro Leu Thr Ser Ser Glu Arg Ile Asp Lys Gln Ile Arg Tyr
 20                  25                  30

ATC CTC GAC GGC ATC TCA GCC CTC CGG AAG GAG ACA TGT GCC ACC TAC       144
Ile Leu Asp Gly Ile Ser Ala Leu Arg Lys Glu Thr Cys Ala Thr Tyr
 35                  40                  45

AAG CTG TGC CAC CCC GAG GAG CTG GTG CTG CTC GGA CAC TCT CTG GGC       192
Lys Leu Cys His Pro Glu Glu Leu Val Leu Leu Gly His Ser Leu Gly
 50                  55                  60

ATC CCC TGG GCT CCC CTG AGC AGC TGC CCC AGC CAG GCC CTG CAG CTG       240
Ile Pro Trp Ala Pro Leu Ser Ser Cys Pro Ser Gln Ala Leu Gln Leu
 65                  70                  75                  80

GCA GGC TGC TTG AGC CAA CTC CAT AGC GGC CTT TTC CTC TAC CAG GGG       288
Ala Gly Cys Leu Ser Gln Leu His Ser Gly Leu Phe Leu Tyr Gln Gly
 85                  90                  95

CTC CTG CAG GCC CTG GAA GGG ATC TCC CCC GAG TTG GGT CCC ACC TTG       336
Leu Leu Gln Ala Leu Glu Gly Ile Ser Pro Glu Leu Gly Pro Thr Leu
100                 105                 110
```

```
GAC ACA CTG CAG CTG GAC GTC GCC GAC TTT GCC ACC ACC ATC TGG CAG      384
Asp Thr Leu Gln Leu Asp Val Ala Asp Phe Ala Thr Thr Ile Trp Gln
115                 120                 125

CAG ATG GAA GAA CTG GGA ATG GCC CCT GCC CTG CAA CCG GAC ACA AAT      432
Gln Met Glu Glu Leu Gly Met Ala Pro Ala Leu Gln Pro Asp Thr Asn
130                 135                 140

GCC AGC CTG CTG ACG AAG CTG CAG GCA CAG AAC CAG TGG CTG CAG GAC      480
Ala Ser Leu Leu Thr Lys Leu Gln Ala Gln Asn Gln Trp Leu Gln Asp
145                 150                 155                 160

ATG ACA ACT CAT CTC ATT CTG CGC AGC TTT AAG GAG TTC CTG CAG TCC      528
Met Thr Thr His Leu Ile Leu Arg Ser Phe Lys Glu Phe Leu Gln Ser
165                 170                 175

AGC CTG AGG GCT CTT CGG CAA ATG TAG                                  555
Ser Leu Arg Ala Leu Arg Gln Met ***
180                 185
```

(2) INFORMATION FOR SEQ ID NO:14:

(i) SEQUENCE CHARACTERISTICS:
        (A) LENGTH:582

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Cell Therapeutics, Inc.

(B) CLONE:

(viii) POSITION IN GENOME:
        (A) CHROMOSOME/SEGMENT:

(B) MAP POSITION:

(C) UNITS:

(ix) FEATURE:
        (A) NAME/KEY:

(B) LOCATION:

(C) IDENTIFICATION METHOD:

(D) OTHER INFORMATION:

(x) PUBLICATION INFORMATION:
   (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:14:

(xi) SEQUENCE DESCRIPTION:SEQ ID NO:14:

```
AAG CTT CCT CTG CCC ATC ACC CCT GTC AAC GCC ACC TGT GCC ATA CGC        48
Lys Leu Pro Leu Pro Ile Thr Pro Val Asn Ala Thr Cys Ala Ile Arg
5                   10                  15

CAC CCA TGT CAC AAC AAC CTC ATG AAC CAG ATC AGG AGC CAA CTG GCA        96
His Pro Cys His Asn Asn Leu Met Asn Gln Ile Arg Ser Gln Leu Ala
20                  25                  30

CAG CTC AAT GGC AGT GCC AAT GCC CTC TTT ATT CTC TAT TAC ACA GCC       144
Gln Leu Asn Gly Ser Ala Asn Ala Leu Phe Ile Leu Tyr Tyr Thr Ala
35                  40                  45

CAG GGG GAG CCG TTC CCC AAC AAC CTG GAC AAG CTA TGT GGC CCC AAC       192
Gln Gly Glu Pro Phe Pro Asn Asn Leu Asp Lys Leu Cys Gly Pro Asn
50                  55                  60

GTG ACG GAC TTC CCG CCC TTC CAC GCC AAC GGC ACG GAG AAG GCC AAG       240
Val Thr Asp Phe Pro Pro Phe His Ala Asn Gly Thr Glu Lys Ala Lys
65                  70                  75                  80

CTG GTG GAG CTG TAC CGC ATA GTC GTG TAC CTT GGC ACC TCC CTG GGC       288
Leu Val Glu Leu Tyr Arg Ile Val Val Tyr Leu Gly Thr Ser Leu Gly
85                  90                  95

AAC ATC ACC CGG GAC CAG AAG ATC CTC AAC CCC AGT GCC CTC AGC CTC       336
Asn Ile Thr Arg Asp Gln Lys Ile Leu Asn Pro Ser Ala Leu Ser Leu
100                 105                 110

CAC AGC AAG CTC AAC GCC ACC GCC GAC ATC CTG CGA GGC CTC CTT AGC       384
His Ser Lys Leu Asn Ala Thr Ala Asp Ile Leu Arg Gly Leu Leu Ser
115                 120                 125

AAC GTG CTG TGC CGC CTG TGC AGC AAG TAC CAC GTG GGC CAT GTG GAC       432
Asn Val Leu Cys Arg Leu Cys Ser Lys Tyr His Val Gly His Val Asp
130                 135                 140

GTG ACC TAC GGT CCG GCG CCC CCG CTG GCG CCC CCC TCC TCA GCC TGG       480
Val Thr Tyr Gly Pro Ala Pro Pro Leu Ala Pro Pro Ser Ser Ala Trp
145                 150                 155                 160

GGG GGC ATC AGG GCC GCC CAC GCC ATC CTG GGG GGC CTG CAC CTG ACA       528
Gly Gly Ile Arg Ala Ala His Ala Ile Leu Gly Gly Leu His Leu Thr
165                 170                 175

CTT GAC TGG GCC GTG AGG GGA CTG CTG CTG CTG AAG ACT CGG CTG TGA       576
Leu Asp Trp Ala Val Arg Gly Leu Leu Leu Leu Lys Thr Arg Leu ***
180                 185                 190
```

```
GGA TCC                                                        582
Gly Ser
194
```

(2) INFORMATION FOR SEQ ID NO:15:

(i) SEQUENCE CHARACTERISTICS:
        (A) LENGTH:549

(B) TYPE:nucleic acid (C) STRANDEDNESS:double stranded (D) TOPOLOGY:linear (ii) MOLECULE TYPE:cDNA to mRNA (iii) HYPOTHETICAL:no (iv) ANTI-SENSE:no (v) FRAGMENT TYPE:

(vi) ORIGINAL SOURCE:
        (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
        (A) LIBRARY:Cell Therapeutics, Inc.

(B) CLONE:

(viii) POSITION IN GENOME:
        (A) CHROMOSOME/SEGMENT:

(B) MAP POSITION:

(C) UNITS:

(ix) FEATURE:
        (A) NAME/KEY:

(B) LOCATION:

(C) IDENTIFICATION METHOD:

(D) OTHER INFORMATION:

(x) PUBLICATION INFORMATION:
        (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:15:

(xi) SEQUENCE DESCRIPTION:SEQ ID NO:15:

```
AAG CTT GTA CCT CCA GGA GAA GAT TCC AAA GAT GTA GCC GCC CCA CAC         48
Lys Leu Val Pro Pro Gly Glu Asp Ser Lys Asp Val Ala Ala Pro His
5                   10                  15

AGA CAG CCA CTC ACC TCT TCA GAA CGA ATT GAC AAA CAA ATT CGG TAC         96
Arg Gln Pro Leu Thr Ser Ser Glu Arg Ile Asp Lys Gln Ile Arg Tyr
20                  25                  30

ATC CTC GAC GGC ATC TCA GCC CTG AGA AAG GAG ACA TGT AAC AAG AGT        144
Ile Leu Asp Gly Ile Ser Ala Leu Arg Lys Glu Thr Cys Asn Lys Ser
35                  40                  45

AAC ATG TGT GAA AGC AGC AAA GAG GCA CTG GCA GAA AAC AAC CTG AAC        192
Asn Met Cys Glu Ser Ser Lys Glu Ala Leu Ala Glu Asn Asn Leu Asn
50                  55                  60

CTT CCA AAG ATG GCT GAA AAA GAT GGA TGC TTC CAA TCT GGA TTC AAT        240
Leu Pro Lys Met Ala Glu Lys Asp Gly Cys Phe Gln Ser Gly Phe Asn
65                  70                  75                  80

GTA TAC CTA GAG TAC CTC CAG AAC AGA TTT GAG AGT AGT GAG GAA CAA        288
Val Tyr Leu Glu Tyr Leu Gln Asn Arg Phe Glu Ser Ser Glu Glu Gln
85                  90                  95

GAG GAG ACT TGC CTG GTG AAA ATC ATC ACT GGT CTT TTG GAG TTT GAG        336
Glu Glu Thr Cys Leu Val Lys Ile Ile Thr Gly Leu Leu Glu Phe Glu
100                 105                 110

GCC AGA GCT GTG CAG ATG AGT ACA AAA GTC CTG ATC CAG TTC CTG CAG        384
Ala Arg Ala Val Gln Met Ser Thr Lys Val Leu Ile Gln Phe Leu Gln
115                 120                 125

AAA AAG GCA AAG AAT CTA GAT GCA ATA ACC ACT CCG GCG CCC CCG CTG        432
Lys Lys Ala Lys Asn Leu Asp Ala Ile Thr Thr Pro Ala Pro Pro Leu
130                 135                 140

GCG CCC CCC TCC TCA GCC TGG GGG GGC ATC AGG GCC GCC CAC GCC ATC        480
Ala Pro Pro Ser Ser Ala Trp Gly Gly Ile Arg Ala Ala His Ala Ile
145                 150                 155                 160

CTG GGG GGG CTG CAC CTG ACA CTT GAC TGG GCC GTG AGG GGA CTG CTG        528
Leu Gly Gly Leu His Leu Thr Leu Asp Trp Ala Val Arg Gly Leu Leu
165                 170                 175

CTG CTG AAG ACT CGG CTG TGA                                            549
Leu Leu Lys Thr Arg Leu ***
180
```

(2) INFORMATION FOR SEQ ID NO:16:

(i) SEQUENCE CHARACTERISTICS:
        (A) LENGTH:537

(B) TYPE:nucleic acid (C) STRANDEDNESS:double stranded (D) TOPOLOGY:linear (ii) MOLECULE TYPE:cDNA to mRNA (iii) HYPOTHETICAL:no

```
    (iv) ANTI-SENSE:no (v) FRAGMENT TYPE:

(vi) ORIGINAL SOURCE:
            (A) ORGANISM:homo sapien (B) STRAIN:

(C) INDIVIDUAL ISOLATE:

(D) DEVELOPMENTAL STAGE:

(E) HAPLOTYPE:

(F) TISSUE TYPE:

(G) CELL TYPE:

(H) CELL LINE:

(I) ORGANELLE:

(vii) IMMEDIATE SOURCE:
            (A) LIBRARY:Cell Therapeutics, Inc.

(B) CLONE:

(viii) POSITION IN GENOME:
            (A) CHROMOSOME/SEGMENT:

(B) MAP POSITION:

(C) UNITS:

(ix) FEATURE:
            (A) NAME/KEY:

(B) LOCATION:

(C) IDENTIFICATION METHOD:

(D) OTHER INFORMATION:

(x) PUBLICATION INFORMATION:
            (A) AUTHORS:

(B) TITLE:

(C) JOURNAL:

(D) VOLUME:

(E) ISSUE:

(F) PAGES:

(G) DATE:

(H) DOCUMENT NUMBER:

(I) FILING DATE:

(J) PUBLICATION DATE:

(K) RELEVANT RESIDUES IN SEQ ID NO:16:

(xi) SEQUENCE DESCRIPTION:SEQ ID NO:16:

AAG CTT ACT CCT CTG GGC CCT GCC AGC TCC CTG CCC CAG AGC TTC CTG        48
Lys Leu Thr Pro Leu Gly Pro Ala Ser Ser Leu Pro Gln Ser Phe Leu
 5                  10                  15
```

-continued

```
CTC AAG TGC TTA GAG CAA GTG AGG AAG ATC CAG GGC GAT GGC GCA GCG     96
Leu Lys Cys Leu Glu Gln Val Arg Lys Ile Gln Gly Asp Gly Ala Ala
 20              25                  30

CTC CAG GAG AAG CTG TGT GCC ACC TAC AAG CTG TGC CAC CCC GAG GAG    144
Leu Gln Glu Lys Leu Cys Ala Thr Tyr Lys Leu Cys His Pro Glu Glu
 35              40                  45

CTG GTG CTG CTC GGA CAC TCT CTG GGC ATC CCC TGG GCT CCC CTG AGC    192
Leu Val Leu Leu Gly His Ser Leu Gly Ile Pro Trp Ala Pro Leu Ser
 50              55                  60

AGC TGC CCC AGC CAG GCC CTG CAG CTG GCA GGC TGC TTG AGC CAA CTC    240
Ser Cys Pro Ser Gln Ala Leu Gln Leu Ala Gly Cys Leu Ser Gln Leu
 65              70                  75              80

CAT AGC GGC CTT TTC CTC TAC CAG GGG CTC CTG CAG GCC CTG GAA GGG    288
His Ser Gly Leu Phe Leu Tyr Gln Gly Leu Leu Gln Ala Leu Glu Gly
 85              90                  95

ATC TCC CCC GAG TTG GGT CCC ACC TTG GAC ACA CTG CAG CTG GAC GTC    336
Ile Ser Pro Glu Leu Gly Pro Thr Leu Asp Thr Leu Gln Leu Asp Val
100             105                 110

GCC GAC TTT GCC ACC ACC ATC TGG CAG CAG ATG GAA GAA CTG GGA ATG    384
Ala Asp Phe Ala Thr Thr Ile Trp Gln Gln Met Glu Glu Leu Gly Met
115             120                 125

GCC CCT GCC CTG CAA CCG GCG CCC CCG CTG GCG CCC CCC TCC TCA GCC    432
Ala Pro Ala Leu Gln Pro Ala Pro Pro Leu Ala Pro Pro Ser Ser Ala
130             135                 140

TGG GGG GGC ATC AGG GCC GCC CAC GCC ATC CTG GGG GGG CTG CAC CTG    480
Trp Gly Gly Ile Arg Ala Ala His Ala Ile Leu Gly Gly Leu His Leu
145             150                 155             160

ACA CTT GAC TGG GCC GTG AGG GGA CTG CTG CTG CTG AAG ACT CGG CTG    528
Thr Leu Asp Trp Ala Val Arg Gly Leu Leu Leu Leu Lys Thr Arg Leu
165             170                 175

TGA GGA TCC    537
*** Gly Ser
179
```

(2) INFORMATION FOR SEQ ID NO:17:

(i) SEQUENCE CHARACTERISTICS:
        (A) LENGTH: 184

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:17:

```
Lys Leu Val Pro Pro Gly Glu Asp Ser Lys Asp Val Ala Ala Pro His
 5                  10                  15

Arg Gln Pro Leu Thr Ser Ser Glu Arg Ile Asp Lys Gln Ile Arg Tyr
 20                  25                  30

Ile Leu Asp Gly Ile Ser Ala Leu Arg Lys Glu Thr Cys Asn Lys Ser
 35                  40                  45
```

-continued

```
Asn Met Cys Glu Ser Ser Lys Glu Ala Leu Ala Glu Asn Asn Leu Asn
 50              55                  60
Leu Pro Lys Met Ala Glu Lys Asp Gly Cys Phe Gln Ser Gly Phe Asn
 65              70                  75                      80
Glu Glu Thr Cys Leu Val Lys Ile Ile Thr Gly Leu Leu Glu Phe Glu
 85              90                  95
Val Tyr Leu Glu Tyr Leu Gln Asn Arg Phe Glu Ser Ser Glu Glu Gln
100             105                 110
Ala Arg Ala Val Gln Met Ser Thr Lys Val Leu Ile Gln Phe Leu Gln
115             120                 125
Lys Lys Ala Lys Asn Leu Asp Ala Ile Thr Thr Pro Asp Pro Thr Gln
130             135                 140
Gly Ala Met Pro Ala Phe Ala Ser Ala Phe Gln Arg Arg Ala Gly Gly
145             150                 155                     160
Val Leu Val Ala Ser His Leu Gln Ser Phe Leu Glu Val Ser Tyr Arg
165             170                 175
Val Leu Arg His Leu Ala Gln Pro
180
```

(2) INFORMATION FOR SEQ ID NO:18:

(i) SEQUENCE CHARACTERISTICS:
        (A) LENGTH: 194

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:18:

```
Lys Leu Pro Leu Pro Ile Thr Pro Val Asn Ala Thr Cys Ala Ile Arg
  5              10                  15
His Pro Cys His Asn Asn Leu Met Asn Gln Ile Arg Ser Gln Leu Ala
 20              25                  30
Gln Leu Asn Gly Ser Ala Asn Ala Leu Phe Ile Leu Tyr Tyr Thr Ala
 35              40                  45
Gln Gly Glu Pro Phe Pro Asn Asn Leu Asp Lys Leu Cys Gly Pro Asn
 50              55                  60
Val Thr Asp Phe Pro Pro Phe His Ala Asn Gly Thr Glu Lys Ala Lys
 65              70                  75                      80
Leu Val Glu Leu Tyr Arg Ile Val Val Tyr Leu Gly Thr Ser Leu Gly
 85              90                  95
Asn Ile Thr Arg Asp Gln Lys Ile Leu Asn Pro Ser Ala Leu Ser Leu
100             105                 110
His Ser Lys Leu Asn Ala Thr Ala Asp Ile Leu Arg Gly Leu Leu Ser
115             120                 125
Asn Val Leu Cys Arg Leu Cys Ser Lys Tyr His Val Gly His Val Asp
130             135                 140
```

```
Val Thr Tyr Gly Pro Asp Pro Thr Thr Asn Ala Ser Leu Leu Thr Lys
145                 150                 155                 160

Leu Gln Ala Gln Asn Gln Trp Leu Gln Asp Met Thr Thr His Leu Ile
165                 170                 175

Leu Arg Ser Phe Lys Glu Phe Leu Gln Ser Ser Leu Arg Ala Leu Arg
180                 185                 190

Gln Met
```

(2) INFORMATION FOR SEQ ID NO:19:

(i) SEQUENCE CHARACTERISTICS:
        (A) LENGTH: 192

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:19:

```
Lys Leu Pro Leu Pro Ile Thr Pro Val Asn Ala Thr Cys Ala Ile Arg
5                   10                  15

His Pro Cys His Asn Asn Leu Met Asn Gln Ile Arg Ser Gln Leu Ala
20                  25                  30

Gln Leu Asn Gly Ser Ala Asn Ala Leu Phe Ile Leu Tyr Tyr Thr Ala
35                  40                  45

Gln Gly Glu Pro Phe Pro Asn Asn Leu Asp Lys Leu Cys Gly Pro Asn
50                  55                  60

Val Thr Asp Phe Pro Pro Phe His Ala Asn Gly Thr Glu Lys Ala Lys
65                  70                  75                  80

Leu Val Glu Leu Tyr Arg Ile Val Val Tyr Leu Gly Thr Ser Leu Gly
85                  90                  95

Asn Ile Thr Arg Asp Gln Lys Ile Leu Asn Pro Ser Ala Leu Ser Leu
100                 105                 110

His Ser Lys Leu Asn Ala Thr Ala Asp Ile Leu Arg Gly Leu Leu Ser
115                 120                 125

Asn Val Leu Cys Arg Leu Cys Ser Lys Tyr His Val Gly His Val Asp
130                 135                 140

Val Thr Tyr Gly Pro Asp Thr Asn Ala Ser Leu Leu Thr Lys Leu Gln
145                 150                 155                 160

Ala Gln Asn Gln Trp Leu Gln Asp Met Thr Thr His Leu Ile Leu Arg
165                 170                 175

Ser Phe Lys Glu Phe Leu Gln Ser Ser Leu Arg Ala Leu Arg Gln Met
180                 185                 190
```

(2) INFORMATION FOR SEQ ID NO:20:

(i) SEQUENCE CHARACTERISTICS:
        (A) LENGTH: 174

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:20:

```
Lys Leu Val Pro Pro Gly Glu Asp Ser Lys Asp Val Ala Ala Pro His
 5              10                  15

Arg Gln Pro Leu Thr Ser Ser Glu Arg Ile Asp Lys Gln Ile Arg Tyr
20                  25                  30

Ile Leu Asp Gly Ile Ser Ala Leu Arg Lys Glu Thr Cys Asn Lys Ser
35                  40                  45

Asn Met Cys Glu Ser Ser Lys Glu Ala Leu Ala Glu Asn Asn Leu Asn
50                  55                  60

Leu Pro Lys Met Ala Glu Lys Asp Gly Cys Phe Gln Ser Gly Phe Asn
65              70                  75                  80

Glu Glu Thr Cys Leu Val Lys Ile Ile Thr Gly Leu Leu Glu Phe Glu
85                  90                  95

Val Tyr Leu Glu Tyr Leu Gln Asn Arg Phe Glu Ser Ser Glu Glu Gln
100                 105                 110

Ala Arg Ala Val Gln Met Ser Thr Lys Val Leu Ile Gln Phe Leu Gln
115                 120                 125

Lys Lys Ala Lys Asn Leu Asp Ala Ile Thr Thr Pro Asp Pro Asp Thr
130                 135                 140

Ser Gly Lys Asp Val Phe Gln Lys Lys Leu Gly Cys Gln Leu Leu
145                 150                 155                 160

Gly Lys Tyr Lys Gln Ile Ile Ala Val Leu Ala Gln Ala Phe
165                 170
```

(2) INFORMATION FOR SEQ ID NO:21:

(i) SEQUENCE CHARACTERISTICS:
        (A) LENGTH: 172

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien

```
    (xi) SEQUENCE DESCRIPTION:SEQ ID NO:21:

Lys Leu Val Pro Pro Gly Glu Asp Ser Lys Asp Val Ala Ala Pro His
5                   10                  15

Arg Gln Pro Leu Thr Ser Ser Glu Arg Ile Asp Lys Gln Ile Arg Tyr
20                  25                  30

Ile Leu Asp Gly Ile Ser Ala Leu Arg Lys Glu Thr Cys Asn Lys Ser
35                  40                  45

Asn Met Cys Glu Ser Ser Lys Glu Ala Leu Ala Glu Asn Asn Leu Asn
50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
85                  90                  95

Val Tyr Leu Glu Tyr Leu Gln Asn Arg Phe Glu Ser Ser Glu Glu Gln
100                 105                 110

Ala Arg Ala Val Gln Met Ser Thr Lys Val Leu Ile Gln Phe Leu Gln
115                 120                 125

Lys Lys Ala Lys Asn Leu Asp Ala Ile Thr Thr Pro Asp Thr Ser Gly
130                 135                 140

Lys Asp Val Phe Gln Lys Lys Leu Gly Cys Gln Leu Leu Gly Lys
145                 150                 155                 160

Tyr Lys Gln Ile Ile Ala Val Leu Ala Gln Ala Phe
165                 170

(2) INFORMATION FOR SEQ ID NO:22:

(i) SEQUENCE CHARACTERISTICS:
        (A) LENGTH: 184

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:22:

Lys Leu Val Pro Pro Gly Glu Asp Ser Lys Asp Val Ala Ala Pro His
5                   10                  15

Arg Gln Pro Leu Thr Ser Ser Glu Arg Ile Asp Lys Gln Ile Arg Tyr
20                  25                  30

Ile Leu Asp Gly Ile Ser Ala Leu Arg Lys Glu Thr Cys Asn Lys Ser
35                  40                  45

Asn Met Cys Glu Ser Ser Lys Glu Ala Leu Ala Glu Asn Asn Leu Asn
50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
85                  90                  95
```

```
Val Tyr Leu Glu Tyr Leu Gln Asn Arg Phe Glu Ser Ser Glu Glu Gln
100             105                 110

Ala Arg Ala Val Gln Met Ser Thr Lys Val Leu Ile Gln Phe Leu Gln
115             120                 125

Lys Lys Ala Lys Asn Leu Asp Ala Ile Thr Thr Pro Asp Pro Asp Gln
130             135                 140

Gly Ala Met Pro Ala Phe Ala Ser Ala Phe Gln Arg Arg Ala Gly Gly
145             150                 155                 160

Val Leu Val Ala Ser His Leu Gln Ser Phe Leu Glu Val Ser Tyr Arg
165             170                 175

Val Leu Arg His Leu Ala Gln Pro
180
```

(2) INFORMATION FOR SEQ ID NO:23:

(i) SEQUENCE CHARACTERISTICS:
        (A) LENGTH: 184

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:23:

```
Lys Leu Val Pro Pro Gly Glu Asp Ser Lys Asp Val Ala Ala Pro His
5                   10                  15

Arg Gln Pro Leu Thr Ser Ser Glu Arg Ile Asp Lys Gln Ile Arg Tyr
20              25                  30

Ile Leu Asp Gly Ile Ser Ala Leu Arg Lys Glu Thr Cys Ala Thr Tyr
35              40                  45

Lys Leu Cys His Pro Glu Glu Leu Val Leu Leu Gly His Ser Leu Gly
50              55                  60

Ile Pro Trp Ala Pro Leu Ser Ser Cys Pro Ser Gln Ala Leu Gln Leu
65              70                  75                  80

Ala Gly Cys Leu Ser Gln Leu His Ser Gly Leu Phe Leu Tyr Gln Gly
85              90                  95

Leu Leu Gln Ala Leu Glu Gly Ile Ser Pro Glu Leu Gly Pro Thr Leu
100             105                 110

Asp Thr Leu Gln Leu Asp Val Ala Asp Phe Ala Thr Thr Ile Trp Gln
115             120                 125

Gln Met Glu Glu Leu Gly Met Ala Pro Ala Leu Gln Pro Asp Thr Asn
130             135                 140

Ala Ser Leu Leu Thr Lys Leu Gln Ala Gln Asn Gln Trp Leu Gln Asp
145             150                 155                 160

Met Thr Thr His Leu Ile Leu Arg Ser Phe Lys Glu Phe Leu Gln Ser
165             170                 175

Ser Leu Arg Ala Leu Arg Gln Met
180
```

(2) INFORMATION FOR SEQ ID NO:24:

(i) SEQUENCE CHARACTERISTICS:
        (A) LENGTH: 191

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:24:

```
Lys Leu Pro Leu Pro Ile Thr Pro Val Asn Ala Thr Cys Ala Ile Arg
 5                  10                  15

His Pro Cys His Asn Asn Leu Met Asn Gln Ile Arg Ser Gln Leu Ala
 20                  25                  30

Gln Leu Asn Gly Ser Ala Asn Ala Leu Phe Ile Leu Tyr Tyr Thr Ala
 35                  40                  45

Gln Gly Glu Pro Phe Pro Asn Asn Leu Asp Lys Leu Cys Gly Pro Asn
 50                  55                  60

Val Thr Asp Phe Pro Pro Phe His Ala Asn Gly Thr Glu Lys Ala Lys
 65                  70                  75                  80

Leu Val Glu Leu Tyr Arg Ile Val Val Tyr Leu Gly Thr Ser Leu Gly
 85                  90                  95

Asn Ile Thr Arg Asp Gln Lys Ile Leu Asn Pro Ser Ala Leu Ser Leu
100                 105                 110

His Ser Lys Leu Asn Ala Thr Ala Asp Ile Leu Arg Gly Leu Leu Ser
115                 120                 125

Asn Val Leu Cys Arg Leu Cys Ser Lys Tyr His Val Gly His Val Asp
130                 135                 140

Val Thr Tyr Gly Pro Ala Pro Pro Leu Ala Pro Ser Ser Ala Trp
145                 150                 155                 160

Gly Gly Ile Arg Ala Ala His Ala Ile Leu Gly Gly Leu His Leu Thr
165                 170                 175

Leu Asp Trp Ala Val Arg Gly Leu Leu Leu Lys Thr Arg Leu
180                 185                 190
```

(2) INFORMATION FOR SEQ ID NO:25:

(i) SEQUENCE CHARACTERISTICS:
        (A) LENGTH: 182

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
    (A) ORGANISM:homo sapien (xi) SEQUENCE DESCRIPTION:SEQ ID NO:25:

```
Lys Leu Val Pro Pro Gly Glu Asp Ser Lys Asp Val Ala Ala Pro His
 5                  10                  15

Arg Gln Pro Leu Thr Ser Ser Glu Arg Ile Asp Lys Gln Ile Arg Tyr
 20                  25                  30

Ile Leu Asp Gly Ile Ser Ala Leu Arg Lys Glu Thr Cys Asn Lys Ser
 35                  40                  45

Asn Met Cys Glu Ser Ser Lys Glu Ala Leu Ala Glu Asn Asn Leu Asn
 50                  55                  60

Leu Pro Lys Met Ala Glu Lys Asp Gly Cys Phe Gln Ser Gly Phe Asn
 65                  70                  75                  80

Val Tyr Leu Glu Tyr Leu Gln Asn Arg Phe Glu Ser Ser Glu Glu Gln
 85                  90                  95

Glu Glu Thr Cys Leu Val Lys Ile Ile Thr Gly Leu Leu Glu Phe Glu
100                 105                 110

Ala Arg Ala Val Gln Met Ser Thr Lys Val Leu Ile Gln Phe Leu Gln
115                 120                 125

Lys Lys Ala Lys Asn Leu Asp Ala Ile Thr Thr Pro Ala Pro Pro Leu
130                 135                 140

Ala Pro Ser Ser Ala Trp Gly Gly Ile Arg Ala Ala His Ala Ile
145                 150                 155                 160

Leu Gly Gly Leu His Leu Thr Leu Asp Trp Ala Val Arg Gly Leu Leu
165                 170                 175

Leu Leu Lys Thr Arg Leu
180
```

(2) INFORMATION FOR SEQ ID NO:26:

(i) SEQUENCE CHARACTERISTICS:
        (A) LENGTH: 176

(B) TYPE: amino acid (D) TOPOLOGY:linear (ii) MOLECULE TYPE:peptide (iii) HYPOTHETICAL:no (iv) ANTI-SENSE:no (v) FRAGMENT TYPE:

(vi) ORIGINAL SOURCE:
        (A) ORGANISM:homo sapien (xi) SEQUENCE DESCRIPTION:SEQ ID NO:26:

```
Lys Leu Thr Pro Leu Gly Pro Ala Ser Ser Leu Pro Gln Ser Phe Leu
 5                  10                  15

Leu Lys Cys Leu Glu Gln Val Arg Lys Ile Gln Gly Asp Gly Ala Ala
 20                  25                  30

Leu Gln Glu Lys Leu Cys Ala Thr Tyr Lys Leu Cys His Pro Glu Glu
 35                  40                  45

Leu Val Leu Leu Gly His Ser Leu Gly Ile Pro Trp Ala Pro Leu Ser
 50                  55                  60
```

```
-continued

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
85                  90                  95

Ile Ser Pro Glu Leu Gly Pro Thr Leu Asp Thr Leu Gln Leu Asp Val
100                 105                 110

Ala Asp Phe Ala Thr Thr Ile Trp Gln Gln Met Glu Glu Leu Gly Met
115                 120                 125

Ala Pro Ala Leu Gln Pro Ala Pro Pro Leu Ala Pro Pro Ser Ser Ala
130                 135                 140

Trp Gly Gly Ile Arg Ala Ala His Ala Ile Leu Gly Gly Leu His Leu
145                 150                 155                 160

Thr Leu Asp Trp Ala Val Arg Gly Leu Leu Leu Leu Lys Thr Arg Leu
165                 170                 175
```

What is claimed is:

1. A hybrid cytokine polypeptide comprising: 1) four α-helical sequences, the α-helical sequences selected from cytokine α-helical sequences, the cytokine being selected from the group consisting of leukemia inhibitory factor (L), granulocyte colony stimulating factor (G), interleukin-6 (I), interleukin-11 (E), ciliary neurotrophic factor (C), and oncostatin-M (O); and 2) three linking sequences, the linking sequences selected from at least a portion of one or more linking sequences from any of the foregoing cytokines, wherein at least one of the four α-helical sequences is derived from a different cytokine than at least one other of the four α-helical sequences.

2. The polypeptide according to claim 1, comprising four α-helical sequences.

3. The polypeptide according to claim 1, wherein each of the four α-helical sequences comprises a corresponding α-helical sequence of any of the cytokines.

4. The polypeptide according to claim 1, wherein hybrid α-helical sequences I, II and III comprise α-helical sequences from the same cytokine and hybrid α-helical sequence IV comprises an α-helical sequence from a different cytokine.

5. The polypeptide according to claim 1, wherein hybrid α-helical sequences II, III and IV comprise α-helical sequences from the same cytokine and hybrid α-helical sequence I comprises an α-helical sequence from a different cytokine.

6. The polypeptide according to claim 1, wherein hybrid α-helical sequences II and III comprise α-helical sequences from the same cytokine.

7. The polypeptide according to claim 1, wherein hybrid α-helical sequences I and IV comprise α-helical sequences from the same cytokine.

8. The polypeptide according to claim 1, wherein hybrid cytokines maintain a relative polarity orientation of hybrid α-helical sequences I–IV corresponding to a natural polarity orientation.

9. The polypeptide according to claim 1, wherein hybrid α-helical sequences I and IV have anti-parallel orientation.

10. The polypeptide according to claim 1, wherein the hybrid cytokine α-helical sequences are selected from the group consisting of:

GGGI; OOOI; LLLI; IIIO; GGGO; OOOG; LLLO; IIIG; GGGL; OOOL; LLLG; IIIL; IGGG; IOOO; ILLL; OIII; OGGG; GOOO; OLLL; GIII; LGGG; LOOO; GLLL; LIII; GLLG; GIIG; IGGI; LOGI; LLII; LLGG; IIGG; EGGG; OOOE; LLLE; IIIE; LEEE; CEEE; ECCC; EEEC; GCCC; CCCE; LLLC; OOOC; IIIC; GCCG; CGGC; LCCC; CCLL; CCII; CGGG; CELI; and ECCE.

11. The polypeptide according to claim 1, wherein the hybrid cytokine α-helical sequences are selected from the group consisting of:

GGLL; GGII; GGOO; GGGI; IGGG; GILO; LOGI; LLII; GGGO; GGGL; OOOG; LLLG; GOOO; OGGG; LGGG and GGGI.

12. The polypeptide according to claim 1, wherein hybrid cytokine α-helical sequences are selected from the group consisting of:

LLLI; LLLIα; IIIL; IIILα; IIIG; and IGGI.

13. A hybrid cytokine polypeptide comprising: 1) three α-helical sequences, the α-helical sequences selected from cytokine α-helical sequences, the cytokine being selected from the group consisting of leukemia inhibitory factor (L), granulocyte colony stimulating factor (G), interleukin-6 (L), interleukin-11 (E), cilia neurotrophic factor (C), and oncostatin-M (O); and 2) two linking sequences, the linking sequences selected from at least a portion of one or more linking sequences from any of the foregoing cytokines, wherein at least one of the three -helical sequences is derived from a different cytokine than αat least one other of the three α-helical sequences.

14. A hybrid cytokine polypeptide comprising 1) four α-helical sequences, the α-helical sequences selected from a cytokine α-helical sequences, the cytokine being selected from the group consisting of leukemia inhibitory factor (L), granulocyte colony stimulating factor (G), interleukin-6 (I), interleukin-11 (E), ciliary neurotrophic factor (C), and oncostatin-M (O); and 2) three linking sequences, the linking sequences selected from at least a portion of one or more linking sequences from any of the foregoing cytokines, wherein at least one of the four α-helical sequences is derived from a different cytokine than at least one other of the four α-helical sequences, said hybrid cytokine having the ability to stimulate the proliferation of the IL-6 dependent cell line 7TD1.

15. A hybrid cytokine polypeptide comprising: 1) three α-helical sequences, the α-helical sequences selected from cytokine α-helical sequences, the cytokine being selected from the group consisting of leukemia inhibitory factor (L), granulocyte colony stimulating factor (G), interleukin-6 (I), interleukin-11 (E), ciliary neurotrophic factor (C), and oncostatin-M (O); and 2) two linking sequences, the linking sequences selected from at least a portion of one or more linking sequences from any of the foregoing cytokines, wherein at least one of the three α-helical sequences is derived from a different cytokine than at least one other of the three α-helical sequences, said hybrid cytokine having the ability to stimulate the proliferation of the IL-6 dependent cell line 7TD1.

16. A DNA molecule that encodes a hybrid cytokine, the hybrid cytokine comprising: 1) four α-helical sequences selected from an α-helical sequence derived from a cytokine, the cytokine being selected from the group consisting of L, G, I, E, C and O; and 2) three linking sequences selected from at least a portion of a linking sequence from any of the foregoing cytokines, wherein at least one of the four α-helical sequences is from a different cytokine than at least one other of the four α-helical sequences, said DNA molecule comprising:
(A) complementary strands;
(B) DNA molecules which hybridize, under conditions of high stringency, to a probe consisting of any of the foregoing DNA molecules or their complementary sequences; and
(C) DNA molecules which would hybridize to the DNA molecules set forth above or a probe derived from a DNA molecule encoding any of the foregoing hybrid cytokines, but for a degeneracy of genetic code.

17. The molecule according to claim 16, comprising four α-helical sequences.

18. The molecule according to claim 16, wherein each of the four α-helical sequences comprises a corresponding α-helical sequence of any of the cytokines.

19. The molecule according to claim 16, wherein hybrid α-helical sequences I, II and III comprise α-helical sequences from the same cytokine and hybrid α-helical sequence IV comprises an α-helical sequence from a different cytokine.

20. The molecule according to claim 16, wherein hybrid α-helical sequences II, III and IV comprise α-helical sequences from the same cytokine and hybrid α-helical sequence I comprises an α-helical sequence from a different cytokine.

21. The molecule according to claim 16, wherein hybrid α-helical sequences II and III comprise α-helical sequences from the same cytokine.

22. The molecule according to claim 16 wherein hybrid α-helical sequences I and IV comprise α-helical sequences from the same cytokine.

23. The molecule according to claim 16, wherein hybrid cytokines maintain a relative polarity orientation of hybrid α-helical sequences I–IV corresponding to a natural polarity orientation.

24. The molecule according to claim 16, wherein hybrid α-helical sequences I and IV have anti-parallel orientation.

25. The molecule according to claim 16, wherein the hybrid cytokine α-helical sequences are selected from the group consisting of:
GGGI; OOOI; LLLI; IIIO; GGGO; OOOG; LLLO; IIIG; GGGL; OOOL; LLLG; IIIL; IGGG; IOOO; ILLL; OIII; OGGG; GOOO; OLLL; GIII; LGGG; LOOO; GLLL; LIII; GLLG; GIIG; IGGI; LOGI; LLII; LLGG; IIGG; EGGG; OOOE; LLLE; IIIE; LEEE; CEEE; ECCC; EEEC; GCCC; CCCE; LLLC; OOOC; IIIC; GCCG; CGGC; LCCC; CCLL; CCII; CGGG; CELI; and ECCE.

26. The molecule according to claim 16, wherein the hybrid cytokine α-helical sequences are selected from the group consisting of:
GGLL; GGII; GGOO; GGGI; IGGG; GILO; LOGI; LLII; GGGO; GGGL; OOOG; LLLG; GOOO; OGGG; LGGG and GGGI.

27. The molecule according to claim 16, wherein the hybrid cytokine α-helical sequences are selected from the group consisting of:
LLLI; LLLIα; IIIL; IIILα; IIIG; and IGGI.

28. A DNA molecule that encodes a hybrid cytokine, the hybrid cytokine comprising: 1) three α-helical sequences selected from an α-helical sequence derived from a cytokine, the cytokine being selected from the group consisting of L, G, I, E, C, O; and 2) three linking sequences selected from at least a portion of a linking sequence from any of the foregoing cytokines, wherein at least one of the three α-helical sequences is from a different cytokine than at least one other of the three α-helical sequences, said DNA molecule comprising:
(A) complementary strands;
(B) DNA molecules which hybridize, under conditions of high stringency, to a probe consisting of any of the foregoing DNA molecules or their complementary sequences; and
(C) DNA molecules which would hybridize to the DNA molecules set forth above, but for a degeneracy of genetic code.

29. A DNA molecule that encodes a hybrid cytokine, the hybrid cytokine comprising 1) four α-helical sequences selected from an α-helical sequence derived from a cytokine, the cytokine being selected from the group consisting of L, G, I, E, C and O; and 2) three linking sequences selected from at least a portion of a linking sequence from any of the foregoing cytokines wherein at least one of the four α-helical sequences is from a different cytokine than at least one other of the four α-helical sequences, said DNA molecule comprising:
(A) complementary strands;
(B) DNA molecules which hybridize, under conditions of high stringency, to a probe consisting of any of the foregoing DNA molecules or their complementary sequences; and
(C) DNA molecules which would hybridize to the DNA molecules set forth above or a probe derived from a DNA molecule encoding any of the foregoing hybrid cytokines, but for a degeneracy of genetic code, and wherein, said hybrid cytokine encoded by said DNA has the ability to stimulate the proliferation of the IL-6 dependent cell line 7TD1.

30. A biologically functional plasmid or viral DNA vector comprising the molecule according to claim 16.

31. An expression system for expressing the hybrid cytokine comprising the molecule of claim 13, operably linked to control sequences and compatible with a recombinant host stably transfected with the molecule.

32. Recombinant host cells transformed with the expression system of claim 31.

33. A method for expressing a hybrid cytokine of claim 1, comprising the steps of:
culturing recombinant host cells transformed with an expression system for expressing the hybrid cytokine comprising the molecule of claim 1, said DNA operably linked to control sequences and compatible with the recombinant host cells, under conditions which effect expression of said hybrid cytokine, and
recovering said hybrid cytokine.

* * * * *